United States Patent
Desai et al.

(10) Patent No.: US 8,927,660 B2
(45) Date of Patent: *Jan. 6, 2015

(54) CROSSLINKABLE POLYISOBUTYLENE-BASED POLYMERS AND MEDICAL DEVICES CONTAINING THE SAME

(71) Applicant: Cardiac Pacemakers, Inc., St. Paul, MN (US)

(72) Inventors: Shrojalkumar Desai, Lake Bluff, IL (US); Mark W. Boden, Harrisville, RI (US)

(73) Assignee: Cardiac Pacemakers Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/975,896

(22) Filed: Aug. 26, 2013

(65) Prior Publication Data

US 2014/0088218 A1    Mar. 27, 2014

Related U.S. Application Data

(62) Division of application No. 12/860,002, filed on Aug. 20, 2010, now Pat. No. 8,529,934.

(60) Provisional application No. 61/235,931, filed on Aug. 21, 2009.

(51) Int. Cl.
| | |
|---|---|
| A61L 31/10 | (2006.01) |
| A61L 27/16 | (2006.01) |
| A61L 27/18 | (2006.01) |
| A61L 31/04 | (2006.01) |
| A61L 31/06 | (2006.01) |
| C08F 10/10 | (2006.01) |
| C08G 18/62 | (2006.01) |
| C08G 18/69 | (2006.01) |
| A61L 31/16 | (2006.01) |
| C08F 110/10 | (2006.01) |

(52) U.S. Cl.
CPC .................. *A61L 31/10* (2013.01); *A61L 27/16* (2013.01); *A61L 27/18* (2013.01); *A61L 31/048* (2013.01); *A61L 31/06* (2013.01); *C08F 10/10* (2013.01); *C08G 18/6204* (2013.01); *C08G 18/69* (2013.01); *A61L 31/16* (2013.01); *C08F 110/10* (2013.01); *C08F 2810/40* (2013.01)
USPC ....................................................... 525/455

(58) Field of Classification Search
None
See application file for complete search history.

(56) References Cited

U.S. PATENT DOCUMENTS

| | | |
|---|---|---|
| 3,328,372 A | 6/1967 | Thomas et al. |
| 3,427,366 A | 2/1969 | Verdol et al. |
| 3,505,252 A | 4/1970 | Brotherton et al. |
| 3,642,964 A | 2/1972 | Rausch et al. |
| 3,755,265 A | 8/1973 | Fletcher et al. |
| 3,815,611 A | 6/1974 | Denniston, III |
| 4,043,331 A | 8/1977 | Martin et al. |
| 4,103,079 A | 7/1978 | Thaler |
| 4,118,427 A | 10/1978 | Rhein et al. |
| 4,276,394 A | 6/1981 | Kennedy et al. |
| 4,316,973 A | 2/1982 | Kennedy |
| 4,342,849 A | 8/1982 | Kennedy |
| 4,352,359 A | 10/1982 | Larimore et al. |
| 4,423,185 A | 12/1983 | Matsumoto et al. |
| 4,477,604 A | 10/1984 | Oechsie, III |
| 4,484,586 A | 11/1984 | McMickle et al. |
| 4,486,572 A | 12/1984 | Kennedy |
| 4,539,996 A | 9/1985 | Engel |
| 4,570,270 A | 2/1986 | Oechsie, III |
| 4,675,361 A | 6/1987 | Ward, Jr. |
| 4,686,137 A | 8/1987 | Ward, Jr. et al. |
| 4,752,626 A | 6/1988 | Hoye et al. |
| 4,767,885 A | 8/1988 | Kennedy |
| 4,771,082 A | 9/1988 | Solodovnik et al. |
| 4,861,830 A | 8/1989 | Ward, Jr. |
| 4,880,883 A | 11/1989 | Grasel et al. |
| 4,888,389 A | 12/1989 | Kennedy et al. |
| 4,906,673 A | 3/1990 | Mori et al. |
| 4,910,321 A | 3/1990 | Kennedy et al. |
| 4,928,689 A | 5/1990 | Hauser |
| 4,939,184 A | 7/1990 | Kennedy |
| 5,000,875 A | 3/1991 | Kolouch |
| 5,017,664 A | 5/1991 | Grasel et al. |

(Continued)

FOREIGN PATENT DOCUMENTS

| | | |
|---|---|---|
| BR | 9003841 | 2/1992 |
| CA | 2278680 | 8/1998 |

(Continued)

OTHER PUBLICATIONS

Ojha et al., Polymer, 2009, vol. 50, pp. 3448-3457.*
Anonymous, "Butyl Rubber Properties and Applications", downloaded from URL: hiit://www.iisrp.com/WebPolymers/02ButylRubberIIR.pdf available on the internet on Jul. 31, 2007 according to Wayback Web Archive.
Ojha, U et al., "Syntheses and characterization of novel biostable polyisobutylene based thermoplastic polyurethanes", Polymer 50 (2009) 3448-3457.

(Continued)

*Primary Examiner* — Brian Gulledge
(74) *Attorney, Agent, or Firm* — Faegre Baker Daniels LLP

(57) ABSTRACT

The present invention pertains to crosslinkable and crosslinked polyisobutylene-based polymers, to compositions that contain such polymers, and to medical devices that are formed using such polymers. According to one aspect, the present invention pertains to crosslinkable and crosslinked compositions that comprise a copolymer that comprises a polyisobutylene segment and two or more reactive groups. According to another aspect, the present invention pertains to medical devices that contain such compositions. According to another aspect, the present invention pertains to methods of making medical devices using such compositions.

11 Claims, No Drawings

(56) References Cited

U.S. PATENT DOCUMENTS

| | | |
|---|---|---|
| 5,026,814 A | 6/1991 | Re et al. |
| 5,029,585 A | 7/1991 | Lieber et al. |
| 5,090,422 A | 2/1992 | Dahl et al. |
| 5,103,837 A | 4/1992 | Weidlich et al. |
| 5,120,813 A | 6/1992 | Ward, Jr. |
| 5,129,404 A | 7/1992 | Spehr et al. |
| 5,149,739 A | 9/1992 | Lee |
| 5,152,299 A | 10/1992 | Soukup |
| 5,194,505 A | 3/1993 | Brugel |
| 5,212,248 A | 5/1993 | Knoll et al. |
| 5,269,810 A | 12/1993 | Hull et al. |
| 5,282,844 A | 2/1994 | Stokes et al. |
| 5,322,520 A | 6/1994 | Milder |
| 5,324,324 A | 6/1994 | Vachon et al. |
| 5,330,520 A | 7/1994 | Maddison et al. |
| 5,332,791 A | 7/1994 | Knoll et al. |
| 5,332,798 A | 7/1994 | Ferreri et al. |
| 5,340,881 A | 8/1994 | Kennedy et al. |
| 5,385,579 A | 1/1995 | Helland |
| 5,428,123 A | 6/1995 | Ward et al. |
| 5,433,730 A | 7/1995 | Alt |
| 5,442,010 A | 8/1995 | Hauenstein et al. |
| 5,442,015 A | 8/1995 | Kennedy et al. |
| 5,476,496 A | 12/1995 | Strandberg et al. |
| 5,554,178 A | 9/1996 | Dahl et al. |
| 5,589,563 A | 12/1996 | Ward et al. |
| 5,609,622 A | 3/1997 | Soukup et al. |
| 5,637,647 A | 6/1997 | Faust |
| 5,663,234 A | 9/1997 | Kennedy et al. |
| 5,677,386 A | 10/1997 | Faust |
| 5,681,514 A | 10/1997 | Woody |
| 5,741,331 A | 4/1998 | Pinchuk |
| 5,755,762 A | 5/1998 | Bush |
| 5,766,527 A | 6/1998 | Schildgen et al. |
| 5,837,313 A | 11/1998 | Ding et al. |
| 5,849,415 A | 12/1998 | Shalaby et al. |
| 5,852,118 A | 12/1998 | Horrion et al. |
| 5,853,652 A | 12/1998 | Schildgen et al. |
| 5,861,023 A | 1/1999 | Vachon |
| 5,874,484 A | 2/1999 | Dirckx et al. |
| 5,898,057 A | 4/1999 | Chiang et al. |
| 5,902,329 A | 5/1999 | Hoffmann et al. |
| 5,931,862 A | 8/1999 | Carson |
| 5,987,746 A | 11/1999 | Williams |
| 5,991,667 A | 11/1999 | Feith |
| 6,005,051 A | 12/1999 | Kennedy et al. |
| 6,010,715 A | 1/2000 | Wick et al. |
| 6,072,003 A | 6/2000 | Horrion et al. |
| 6,093,197 A | 7/2000 | Bakula et al. |
| 6,117,554 A | 9/2000 | Shalaby et al. |
| 6,200,589 B1 | 3/2001 | Kennedy et al. |
| 6,228,945 B1 | 5/2001 | Kennedy et al. |
| 6,236,893 B1 | 5/2001 | Thong |
| 6,242,058 B1 | 6/2001 | Bahadur et al. |
| 6,253,110 B1 | 6/2001 | Brabec et al. |
| 6,256,541 B1 | 7/2001 | Heil et al. |
| 6,284,682 B1 | 9/2001 | Troczynski et al. |
| 6,361,780 B1 | 3/2002 | Ley et al. |
| 6,363,286 B1 | 3/2002 | Zhu et al. |
| 6,365,674 B1 | 4/2002 | Kaufhold et al. |
| 6,426,114 B1 | 7/2002 | Troczynski et al. |
| 6,444,334 B1 | 9/2002 | Doi et al. |
| 6,545,097 B2 | 4/2003 | Pinchuk et al. |
| 6,555,619 B1 | 4/2003 | Kennedy et al. |
| 6,600,956 B2 | 7/2003 | Maschino et al. |
| 6,627,724 B2 | 9/2003 | Meijs et al. |
| 6,709,514 B1 | 3/2004 | Hossainy |
| 6,730,324 B2 | 5/2004 | Troczynski et al. |
| 6,770,325 B2 | 8/2004 | Troczynski et al. |
| 6,827,881 B2 | 12/2004 | Molnar et al. |
| 6,849,667 B2 | 2/2005 | Haseyama et al. |
| 6,870,024 B2 | 3/2005 | Haubennestel et al. |
| 6,889,092 B2 | 5/2005 | Zhu et al. |
| 6,896,965 B1 | 5/2005 | Hossainy |
| 7,013,182 B1 | 3/2006 | Krishnan |
| 7,065,411 B2 | 6/2006 | Verness |
| 7,101,956 B2 | 9/2006 | Benz et al. |
| 7,105,622 B2 | 9/2006 | Kennedy et al. |
| 7,115,300 B1 | 10/2006 | Hossainy |
| 7,174,221 B1 | 2/2007 | Chen et al. |
| 7,196,142 B2 | 3/2007 | Kennedy et al. |
| 7,231,259 B2 | 6/2007 | Jenney et al. |
| 7,247,364 B2 | 7/2007 | Hossainy et al. |
| 7,279,175 B2 | 10/2007 | Chen et al. |
| 7,280,875 B1 | 10/2007 | Chitre et al. |
| 7,289,856 B1 | 10/2007 | Karicherla |
| 7,292,890 B2 | 11/2007 | Whitehurst et al. |
| 7,347,751 B2 | 3/2008 | Sweeney et al. |
| 7,358,306 B2 | 4/2008 | Turri et al. |
| 7,504,052 B2 | 3/2009 | Ehbing et al. |
| 7,553,546 B1 | 6/2009 | Tan |
| 7,617,004 B2 | 11/2009 | Bartels et al. |
| 7,715,922 B1 | 5/2010 | Tan |
| 7,756,589 B2 | 7/2010 | Krishnan |
| 7,881,808 B2 | 2/2011 | Borgaonkar et al. |
| 7,979,142 B2 | 7/2011 | Krishnan |
| 8,324,290 B2 | 12/2012 | Desai et al. |
| 8,372,468 B2 | 2/2013 | Desai et al. |
| 8,374,704 B2 | 2/2013 | Desai et al. |
| 8,501,831 B2 | 8/2013 | Desai et al. |
| 8,529,934 B2 | 9/2013 | Desai et al. |
| 8,644,952 B2 | 2/2014 | Desai et al. |
| 8,660,663 B2 | 2/2014 | Wolf et al. |
| 2002/0012694 A1* | 1/2002 | Moo-Young et al. ......... 424/449 |
| 2002/0022826 A1 | 2/2002 | Reynolds et al. |
| 2002/0138123 A1 | 9/2002 | Casas-Bejar et al. |
| 2003/0031699 A1 | 2/2003 | Van Antwerp |
| 2003/0073961 A1 | 4/2003 | Happ |
| 2003/0093136 A1 | 5/2003 | Osypka et al. |
| 2003/0125499 A1 | 7/2003 | Benz et al. |
| 2003/0204022 A1 | 10/2003 | Kennedy et al. |
| 2004/0037886 A1 | 2/2004 | Hsu |
| 2004/0054210 A1 | 3/2004 | Benz et al. |
| 2004/0063805 A1 | 4/2004 | Pacetti et al. |
| 2004/0068036 A1 | 4/2004 | Halladay et al. |
| 2004/0186545 A1 | 9/2004 | Rosero et al. |
| 2004/0198901 A1 | 10/2004 | Graham et al. |
| 2005/0031874 A1 | 2/2005 | Michal et al. |
| 2005/0037050 A1* | 2/2005 | Weber ........................ 424/426 |
| 2005/0060022 A1 | 3/2005 | Felt et al. |
| 2005/0070985 A1 | 3/2005 | Knapp et al. |
| 2005/0080470 A1 | 4/2005 | Westlund et al. |
| 2005/0180919 A1 | 8/2005 | Tedeschi |
| 2005/0288476 A1 | 12/2005 | Yilgor et al. |
| 2006/0047083 A1 | 3/2006 | Yilgor et al. |
| 2006/0223946 A1 | 10/2006 | Faust et al. |
| 2006/0235499 A1 | 10/2006 | Heil, Jr. et al. |
| 2006/0264577 A1 | 11/2006 | Faust et al. |
| 2007/0051531 A1 | 3/2007 | Borgaonkar et al. |
| 2007/0093604 A1 | 4/2007 | Kennedy et al. |
| 2007/0128246 A1 | 6/2007 | Hossainy et al. |
| 2007/0190104 A1 | 8/2007 | Kamath et al. |
| 2007/0203302 A1 | 8/2007 | Kennedy et al. |
| 2007/0282411 A1 | 12/2007 | Franz et al. |
| 2008/0009939 A1 | 1/2008 | Gueriguian et al. |
| 2008/0051866 A1 | 2/2008 | Chen et al. |
| 2008/0167423 A1 | 7/2008 | Richards et al. |
| 2008/0167710 A1 | 7/2008 | Dave et al. |
| 2009/0054961 A1 | 2/2009 | Borgaonkar et al. |
| 2009/0187162 A1 | 7/2009 | Ohara et al. |
| 2009/0292094 A1 | 11/2009 | Larichev et al. |
| 2009/0326077 A1 | 12/2009 | Desai et al. |
| 2010/0002310 A1 | 1/2010 | George et al. |
| 2010/0025703 A1 | 2/2010 | Towns et al. |
| 2010/0055470 A1 | 3/2010 | Klun et al. |
| 2010/0069578 A1 | 3/2010 | Faust et al. |
| 2010/0075018 A1 | 3/2010 | Desai et al. |
| 2010/0107967 A1 | 5/2010 | Tanaka et al. |
| 2010/0179298 A1 | 7/2010 | Faust et al. |
| 2010/0241204 A1 | 9/2010 | Scheuermann |
| 2010/0241208 A1 | 9/2010 | Pinchuk |
| 2010/0241209 A1 | 9/2010 | Krishnan |
| 2011/0045030 A1 | 2/2011 | Desai et al. |
| 2011/0051581 A1 | 3/2011 | Janik et al. |

(56) References Cited

U.S. PATENT DOCUMENTS

| | | |
|---|---|---|
| 2011/0054580 A1 | 3/2011 | Desai et al. |
| 2011/0054581 A1 | 3/2011 | Desai et al. |
| 2011/0087317 A1 | 4/2011 | Borgaonkar et al. |
| 2012/0077934 A1 | 3/2012 | Faust et al. |
| 2012/0158107 A1 | 6/2012 | Wolf et al. |
| 2013/0013040 A1 | 1/2013 | Desai et al. |
| 2013/0041442 A1 | 2/2013 | Arnholt et al. |
| 2013/0079487 A1 | 3/2013 | Faust et al. |
| 2013/0122185 A1 | 5/2013 | Desai et al. |
| 2013/0131765 A1 | 5/2013 | Polkinghorne et al. |
| 2014/0074201 A1 | 3/2014 | Arnholt et al. |
| 2014/0144580 A1 | 5/2014 | Desai et al. |
| 2014/0194963 A1 | 7/2014 | Desai et al. |

FOREIGN PATENT DOCUMENTS

| | | |
|---|---|---|
| CN | 1221430 A | 6/1999 |
| CN | 1248606 | 3/2000 |
| DE | 19610350 A1 | 9/1997 |
| EP | 0153520 | 9/1985 |
| EP | 0259492 | 8/1987 |
| EP | 0610714 A2 | 8/1994 |
| EP | 0732349 | 9/1996 |
| EP | 0837097 | 4/1998 |
| EP | 0961796 | 12/1999 |
| EP | 1061092 | 12/2000 |
| EP | 1489109 A2 | 12/2004 |
| EP | 2006328 | 12/2008 |
| JP | H02-088614 | 3/1990 |
| JP | 4154815 A | 5/1992 |
| JP | 6345821 A | 12/1994 |
| JP | 7102017 A | 4/1995 |
| JP | 7330591 A | 12/1995 |
| JP | H07-331223 | 12/1995 |
| JP | 1087726 A | 4/1998 |
| JP | 11131325 | 5/1999 |
| JP | 11131325 A | 5/1999 |
| JP | 2000169814 A | 6/2000 |
| JP | 2001011319 A | 1/2001 |
| JP | 2001040064 A | 2/2001 |
| JP | 2001131879 A | 5/2001 |
| JP | 2002348317 A | 12/2002 |
| JP | 2004-204181 | 7/2004 |
| JP | 2006515795 A | 6/2006 |
| JP | 2008238761 | 10/2008 |
| WO | 8704625 | 8/1987 |
| WO | 9322360 | 11/1993 |
| WO | 9526993 | 10/1995 |
| WO | WO9700293 A1 | 1/1997 |
| WO | 9747664 | 12/1997 |
| WO | 9833832 | 8/1998 |
| WO | WO9834678 A1 | 8/1998 |
| WO | WO0213785 A2 | 2/2002 |
| WO | WO03042273 A1 | 5/2003 |
| WO | WO2004014453 A1 | 2/2004 |
| WO | 2004044012 | 5/2004 |
| WO | WO2004113400 A2 | 12/2004 |
| WO | WO2005035655 A1 | 4/2005 |
| WO | WO2006011647 A1 | 10/2006 |
| WO | WO2006110647 A1 | 10/2006 |
| WO | WO2007030722 A1 | 3/2007 |
| WO | 2007/119687 A1 | 10/2007 |
| WO | WO2007117566 A2 | 10/2007 |
| WO | WO2007126806 A1 | 11/2007 |
| WO | 2008060333 | 5/2008 |
| WO | 2008066914 | 6/2008 |
| WO | WO2008112190 A1 | 9/2008 |
| WO | WO2008127730 A1 | 10/2008 |
| WO | 2008156806 | 12/2008 |
| WO | WO2009051945 A1 | 4/2009 |
| WO | 2009058397 | 5/2009 |
| WO | 2009158600 | 12/2009 |
| WO | WO2009158609 A1 | 12/2009 |
| WO | WO2010039986 A1 | 4/2010 |
| WO | 2010/081132 A1 | 7/2010 |
| WO | WO2010078552 A1 | 7/2010 |
| WO | WO2010081132 A1 | 7/2010 |
| WO | WO2010111280 A1 | 9/2010 |
| WO | WO2011022583 A1 | 2/2011 |
| WO | WO2011060161 A1 | 5/2011 |

OTHER PUBLICATIONS

Suresh K. Jewrajka et al., "Polyisobutylene-Based Segmented Polyureas. I. Synthesis of Hydrolytically and Oxidatively Stable Polyureas", Journal of Polymer Science: Part A: Polymer Chemistry, vol. 47, 38-48 (2009).

Suresh K. Jewrajka et al., "Polyisobutylene-Based Polyurethanes. II. Polyureas Containing Mixed PIB/PTMO Soft Segments", Journal of Polymer Science: Part A.: Polymer Chemistry, vol. 47, 2787-2797 (2009).

J.A. Miller et al., "New directions in Polyurethane research", Organic Coatings and Applied Polymer Science Proceedings (1982), Am. Chem. Soc., 1982, vol. 47, 124-129.

Kennedy, "Synthesis, characterization and properties of polyisobutylene-based polyurethanes", 6th International SPI Technical/Marketing Conference: Polyurethane—New Paths to Progress—Marketing—Technology Journal of Cellular Plastics, 1983, 514-516.

Macias et al., "Preparacion y reticulacion de polisobutilenos de bajo peso molecular con groupos terminales reactivos", Revista de Plasticos Modernos, Num. 322 (Abril 1983), 412-418.

Giusti et al., "Synthesis and Characterization of New Potentially Hemocompatible Thermoplastic Elastomers", Proc. IUPAC, I.U.P.A. C., Macromol. Symp., 28th (1982). 371.

Mitzner et al., "Modification of segmented Poly(Ether Urethanes) by incorporation of Poly (Isobutylene)Glycol", J.M.S.—Pure Appl. Chem., A34(1), pp. 165-178 (1997).

Mulller et al., "Surface modification of polyurethanes by multicomponent polyaddition reaction", Journal of Materials Science Letters 17 (1998) 115-118.

Weisberg et al., "Synthesis and Characterization of Amphiphilic Poly(urethaneura)-comb-polyisobutylene Copolymers", Macromolecules 2000, 33, 4380-4389.

S.V. Ranade et al., "Styrenic Block Copolymers for Biomaterial and Drug Delivery Applications", Acta. Biomater. Jan. 2005; 1(1): 137-44.

R. Virmani et al., Circulation Feb. 17, 2004, 109(6) 701-5.

E. Mitzner et al., J. Biomater. Sci. Polymer Edn. 1996, 7(12) 1105-1118.

M. Yang et al., J. Biomed. Mater. Res. 48 (1999) 13-23.

C. Jenney, J. Tan, A. Karicherla, J. Burke, and J. Helland, "A New Insulation Material for Cardiac Leads with Potential for Improved Performance," HRS 2005, HeartRhythm, 2, S318-S319 (2005).

J. Tan and C. Jenney, "In Vivo Biostability Study of a New Lead Insulation Material," Cardiostim 2006, Europace Supplements, 8, 179PW/9 (2006).

M. Weißmüller et al., "Preparation and end-linking of hydroxyl-terminated polystyrene star macromolecules," Macromolecular Chemistry and Physics 200(3), 1999, 541-551.

J.P. Kennedy et al., Designed Polymers by Carbocationic Macromolecular Engineering: Theory and Practice, Hanser Publishes 1991, pp. 191-193 and 226-233.

Priyadarsi De and Rodolf Faust, "Carbocationic Polymerization of Isobutylene Using Methylaluminum Bromide Coinitiators: Synthesis of Bromoallyl Functional Polyisobutylene" Macromolecules 2006, 39, 7527-7533.

Priyadarsi De and Rudolf Faust, "Relative Reactivity of C4 Olefins toward the Polyisobutylene Cation" Macromolecules 2006, 29, 6861-6870.

Umaprasana Ojha and Rudolf Faust, "Synthesis and Characterization of Endfunctionalized Polyisobutylenes for Sharpless-type Click Reactions" Polymer Preprints 2007, 48(2), 786.

Rajkhowa, Ritimoni and Faust, Rudolf. "Efficient syntheses of hydroxyallyl end functional polyisobutylenes, a precursor to thermoplastic polyurethanes," Polymer Preprints, V.48(2), 2007, p. 233.

(56) References Cited

OTHER PUBLICATIONS

Joseph P. Kennedy, "Synthesis, Characterization and Properties of Polyisobutylene-Based Polyurethanes" Journal of Elastomers and Plastics 1985 17:82-88.
James I. Wright, "Using Polyurethanes in Medical Applications," 5 pages. Downloaded from http://www.cmdm.com or Oct. 17, 2006.
C. Tonelli et al., "New Fluoro-Modified Thermoplastic Polyrethanes" Journal of Applied Polymer Science, vol. 87 Issue 14 (2003) 2279-2294.
Feng Wang et al., "Polydimethylsiloxane Modification of Segmented Thermoplastic Polyurethanes and Polyureas," Dissertation, Doctor of Philosophy in Chemistry, Virginia Polytechnic Institute and State University, Chapters 1 and 2, Apr. 13, 1998, pp. 1-70.
Michael J. Wiggins et al., "Effect of soft-segment chemistry on polyurethane biostability during in vitro fatgue loading" Journal of biomedical materials research, 68(4), 2004, 668-683.
T.A. Speckhard et al., "Properties of polyisobutylene polyurethane block copolymers: 3. Hard segments based on 4,4'-dicyclohexylemethane diisocyanate (H,,MDI) and butane diol" Polymer, 26 (1985) 70-78.
T.A. Speckhard et al., "Properties of Polyisobutylene-Polyurethane Block Copolymers: I. Macroglycols from Ozonoloysis of Isobutylene-Isoprene Copolymer" Polymer Engineering Science, vol. 23(6), pp. 337-349 (1983).
T.A. Speckhard et al. "Properties of polyisobutylene polyurethane block copolyers: 2. Macroglycols produced by the "inifer" technique" Polymer, vol. 26(1), pp. 55-78, Jan. 1985.
Speckhard et al., "Ultimate Tensile Properties of Segmented Polyurethane Elastomers," Rubber Chem. Technol., 59, 405-431 (1986).
M. Ako et al., "Polyisobutylene-based urethane foams", Polymer Bulletin, vol. 19, No. 2/Feb. 1988, 137-143.
M. Ako et al. "Polyisobutylene-based urethane foams. II. Synthesis and properties of novel polyisobutylene-based flexible polyurethane foams," Journal of Applied Polymer Science, vol. 37, Issue 5 (1988) pp. 1351-1361.
J.E. Puskas et al., "Polyisobutylene-based biomaterials," Journal of Polymer Science Part A: Polymer Chemistry, vol. 42, Issue 13 (2004) pp. 3091-3109.
J. Yeh et al., "Moisture diffusivity of Biomer versus Biomer-coated polyisobutylene polyurethane urea (PIB-PUU): a potential blood sac material for the artificial heart," Journal of Materials Science Letters, vol. 13, No. 19/Jan. 1994, 1390-1391.
B. Ivan, J.P. Kennedy, "Synthesis of New Polyisobutylene-Based Polyurethanes," Am. Chem. Soc., Div. Org. Coat. Plast. Prepr., 43, 909-913 (1980).
J.P. Kennedy, B. Ivan, V.S.C. Chang, "Polyisobutylene-Based Diols and Polyurethanes a) Urethane Chemistry and Applications," Ed.: K.H. Edwards, ACS Symp. Book Series, 172, Washington, D.C., 1981, pp. 383-391.
J.P. Kennedy, B. Ivan, V.S.C. Chang, "Polyisobutylene-Based Diols and Polyurethanes" Advances in Urethane Science and Technology, vol. 8, eds.: K.C. Frisch, D. Klempner, Technomic Publ. Co., Westport USA, 1981, pp. 245-251.
R. Xu et al., "Low permeability biomedical polyurethane nanocomposites" J. Biomed. Mater. Res. 64A (2003) 114-119.
V.S.C. Chang et al., Gas Permeability, Water Adsorption, Hydrolytic Stability and Air-Oven Aging of Polyisobutylene-Based Polyurethane Networks Polymer Bulletin 8 69-74 (1982).
S. Ranade et al., "Physical characterization of controlled release of paclitaxel from the TAXUS Express2 drug-eluting stent," Journal of Biomedical Materials Research Part A. 71A (2004) 625-634.
Kennedy, et al., "Polyisobutylene-based model urethane networks. I. Initial characterization and physical properties" Polymeric Materials Science and Engineering (1983), 49 69-73.
Miyabayashi et al., "Characterization of polyisobutylene-based model urethane networks" Journal of Applied Polymer Science (1986), 31(8), 2523-32.
Kennedy, "Polyurethanes based on polyisobutylenes" CHEMTECH (1986), 16(11), 694-7.
Kennedy et al., "Synthesis, characterization, and properties of novel polyisobutylene-based urethane model networks" Journal of Applied Polymer Science (1987), 33(7), 2449-65.
Yoon et al., "Surface and bulk structure of segmented poly(ether urethanes) with perfluoro chain extenders. 5. Incorporation of poly(dimethylsiloxane) and polyisobutylene macroglycols." Macromolecules (1994), 27(6), 1548-54.
Speckhard et al., "Properties of Polyisobutylene-polyurethane block copolymers." Journal of Elastomers & Plastics (1983), 15(3), 183-92.
Speckhard et al., "New generation polyurethanes." Polymer News (1984), 9(12), 354-8.
Wu et al., "The role of adsorbed fibrinogen in platelet adhesion to polyurethane surfaces: A comparison of surface hydrophobicity, protein adsorption, monoclonal antibody binding, and platelet adhesion." Journal of Biomedical Materials Research, Part A., vol. 74A, Issue 4, pp. 722-738 (2005).
Kennedy, "Synthesis, characterization and properties of polyisobutylene-based polyurethanes", 6th International SPI Technical/Marrketing Conference: Polyurethane—New Paths to Progress—Marketing—Technology Journal of Cellular Plastics 1983 19:288-307.
Bela et al., Living Carbocation Polymerization. XX. Synthesis of Allyl-Telechelic Polyisobutylenes by One-Pot Polymerization-Functionalization polymer. Mater. Sci. Eng. 1988; 58:869-872.
Chen, Chi-Chang et al., "Solid Polymer Electrolytes III Preparation, Characterization, and Ionic Conductivity of New Gelled Polymer Electrolytes Based on Segmented, Perfluoropolyether-Modified Polyurethane", Journal of Polymer Science: Part A: Polymer Chemistry, vol. 40, pp. 486-495 (2002).
Cozzens, David et al., "Long term in vitro biostability of segmented polyisobutylene-based thermoplastic polyurethanes", Journal of Biomedicals Materials Research Journal, 2010, pp. 1-9.
Erdodi, G., et al., "Polyisobutylene-Based Polyurethanes. III. Polyurethanes Containing PIB/PTMO Soft Co-Segments," J. Polym. Sci., Part A: Polym. Chem, 47:5278-5290 (2009).
Erdodi, G., et al., "Polyisobutylene-Based Polyurethanes. VI. Unprecedented Combination of Mechanical Properties and Oxidative/Hydrolytic Stability by H-Bond Acceptor Chain Extenders" J. Polym. Sci., Part A: Polym. Chem, 48:2361-2371 (2010).
Faust, R. et al., "Method to Prepare Block Copolymers by the Combination of Cationic and Anionic Polymerization", U.S. Appl. No. 12/225,905, filed Apr. 5, 2007.
Gadkari A. et al., "Preparation and biocompatibility of Novel Polar-Nonpolar Networks. Osynthesis, Characterization and Histological-Bacterial Analysis of Mixed Polytetrahydrofuran-Polyisobutylene Networks", Polymer Bulletin, vol. 22, No. 1, Jul. 1, 1989, pp. 25-32.
Gunatillake, P.A. et al., "Poly(dimethylsiloxane)/Poly(hexamethylene oxide) Mixed Macrodiol Based Polyurethane Elastomers. I. Synthesis and Properties", Journal of Appl. Polym. Sci. 2000, 76, 2026-2040, © 2000.
Higashihara, T. et al., "Synthesis of Poly(isobutylene-block-methyl methacrylate) by a Novel Coupling Approach", Macromolecules, 39:5275-5279 (2006).
International Preliminary Report on Patentability, Chapter II, issued in PCT/US2006/035064, dated Sep. 12, 2007, 12 pages.
International Search Report and Written Opinion issued in PCT/US2006/013308, dated Aug. 25, 2006.
International Search Report and Written Opinion issued in PCT/US2006/035064, mailed Jan. 23, 2007, 12 pages.
International Search Report and Written Opinion issued in PCT/US2007/007558, mailed Sep. 20, 2007.
International Search Report and Written Opinion issued in PCT/US2007/008528, dated Oct. 2, 2007.
International Search Report and Written Opinion issued in PCT/US2007/012948, dated Nov. 28, 2007.
International Search Report and Written Opinion issued in PCT/US2010/028334, Dated May 6, 2010, 12 pages.
International Search Report and Written Opinion issued in PCT/US2010/047633, Dated Jun. 17, 2011, 12 pages.
International Search Report and Written Opinion issued in PCT/US2010/047633, Jun. 17, 2011, 12 pages.
International Search Report and Written Opinion issued in PCT/US2010/047703, Dated Jun. 17, 2011, 12 pages.

(56) References Cited

OTHER PUBLICATIONS

International Search Report and Written Opinion issued in PCT/US2010/047703, mailed Jun. 17, 2011, 12 pages.
International Search Report and Written Opinion issued in PCT/US2011/061692, mailed Feb. 9, 2012, 9 pages.
International Search Report and Written Opinion issued in PCT/US2013/053448, mailed Apr. 28, 2014, 11 pgs.
International Search Report issued in PCT/US2009/048827, mailed Oct. 6, 2009, 3 pages.
International Search Report issued in PCT/US2009/048845, mailed Oct. 6, 2009, 3 pages.
International Search Report issued in PCT/US2010/020733, mailed May 6, 2010.
Ioffe, David et al., "Bromine, Organic Compounds", Kirk-Othmer Encyclopedia of Chemical Technology, vol. 4, pp. 340-365, © 2002.
Kang, Jungmee et al, "PIB-Based Polyurethanes. IV. The Morphology of Polyurethanes Containing Soft Co-Segments", Journal of Polymer Science Part A: Polymer Chemistry, vol. 47, 6180-6190 (2009).
Kang, Jungmee et al., "Rendering Polyureas Melt Processible", Journal of Polymer Science Part A: Polymer Chemistry, vol. 49, 2461-2467 (2011).
Kang, Jungmee et al., Polyisobutylene-Based Polyurethanes. V. Oxidative-Hydrolytic Stability and Biocampatibility, Journal of Polymer Science: Part A: Polymer Chemistry, vol. 48, 2194-2203 (2010).
Kirby, Darren, "Use of a Bioactive Material on a Pacemaker Electrode for the Purpose of Enhancing Heart Pace/Sense Efficiency", MSC Biomedical Engineering, Thesis, Trinity College Dublin (2003).
Lelah, M.D. et al., "Polyurethanes in Medicine", CRC Press, Boca Raton, FL 1986, Chapter 3.
Li, J. et al., "Polyisobutylene supports—a non-polar hydrocarbon analog of PEG supports", Tetrahedron, 61 (51):12081-12092, Dec. 2005.
Non-Final Office Action issued in U.S. Appl. No. 11/400,059, mailed Apr. 11, 2011.
Non-Final Office Action issued in U.S. Appl. No. 12/492,483, mailed Nov. 21, 2011, 11 pages.
Non-Final Office Action, issued in U.S. Appl. No. 12/685,858, mailed Feb. 15, 2012, 18 pages.
Notice of Allowance issued in U.S. Appl. No. 12/492,483, mailed Jul. 13, 2012, 9 pages.
Office Action issued in EP 07754128 mailed Mar. 31, 2010.
Office Action issued in EP Application No. 07754128.2, Mailed Feb. 19, 2009, 3 pages.
Office Action issued in U.S. Appl. No. 11/400,059, mailed Aug. 24, 2010.
Ojha et al., "Synthesis and Characterization of Thermoplastic Polyurethaneureas based on Polyisobutylene and Poly (tetramethylene oxide) Segments", J. Macromolecular Science, Part A, vol. 47(3), pp. 186-191, Mar. 2010.
Response filed Aug. 31, 2009 to Office Action dated Feb. 19, 2009, EP App 07754128.
Santos, R. et al., "New Telechelic Polymers and Sequential Copolymers by Polyfunctional Initiator-Transfer-Agents (Inifers)", Polymer Bulletin, 11:341-348 (1984).
Simmons, Anne. et al., "The effect of sterilisation on a poly(dimethylsiloxane)/poly(hexamethylene oxide) mixed macrodiol-based Polyurethane elastomer", Biomaterials 2006, 27, 4484-4497.
Tonelli, Claudio et al., "New Perfluoropolyether Soft Segment Containing Polyurethanes", Journal of Applied Polymer Science, vol. 57, pp. 1031-1042 (1995).
Wohlfarth, C., "Permittivity (Dielectric Constant) of Liquids", CRC Handbook, 91st ed. 2010-2011, p. 6-186 to 6-207.
York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.
International Search Report and Written Opinion issued in PCT/US2010/046072, mailed Oct. 15, 2010, 10 pages.

\* cited by examiner

CROSSLINKABLE POLYISOBUTYLENE-BASED POLYMERS AND MEDICAL DEVICES CONTAINING THE SAME

RELATED APPLICATIONS

This present application is a divisional of U.S. patent application Ser. No. 12/860,002, filed Aug. 20, 2010, the disclosure of which is hereby incorporated by reference in its entirety, and which claims the benefit of U.S. provisional application 61/235,931, filed Aug. 21, 2009, which is incorporated by reference herein in its entirety.

FIELD OF THE INVENTION

The present invention relates to crosslinkable polyisobutylene-based polymers and to medical devices containing the same.

BACKGROUND OF THE INVENTION

The use of polymeric materials in medical devices for implantation or insertion into the body of a patient is common in the practice of modern medicine. For example, polymeric materials such as silicone rubber, polyurethane, and fluoropolymers, for instance, polytetrafluoroethylene (PTFE), expanded PTFE (ePTFE) and ethylene tetrafluoroethylene (ETFE), are used as coating materials/insulation for medical leads, providing mechanical protection, electrical insulation, or both.

As another example, drug eluting stents are known which have polymeric coatings over the stent to release a drug to counteract the effects of in-stent restenosis. Specific examples of drug eluting coronary stents include commercially available stents from Boston Scientific Corp. (TAXUS, PROMUS), Johnson & Johnson (CYPHER), and others. See S. V. Ranade et al., Acta Biomater. 2005 January; 1(1): 137-44 and R. Virmani et al., Circulation 2004 Feb. 17, 109(6) 701-5. Various types of polymeric materials have been used in such polymeric coatings including, for example, homopolymers such as poly(n-butyl methacrylate) and copolymers such as poly(ethylene-co-vinyl acetate), poly(vinylidene fluoride-co-hexafluoropropylene), and poly(isobutylene-co-styrene), for example, poly(styrene-b-isobutylene-b-styrene) triblock copolymers (SIBS), which are described, for instance, in U.S. Pat. No. 6,545,097 to Pinchuk et al. SIBS triblock copolymers have a soft, elastomeric low glass transition temperature (Tg) midblock and hard elevated Tg endblocks. SIBS copolymers are thermoplastic elastomers and are highly biocompatible.

SUMMARY OF THE INVENTION

The present invention pertains to crosslinkable and crosslinked polyisobutylene-based polymers, to compositions that contain such polymers, and to medical devices that are formed using such polymers.

According to one aspect, the present invention pertains to crosslinkable and crosslinked compositions that comprise a copolymer that comprises a polyisobutylene segment and two or more reactive groups.

According to another aspect, the present invention pertains to medical devices that contain such compositions.

According to another aspect, the present invention pertains to methods of making medical devices using such compositions.

Among other benefits, crosslinking imparts improved abrasion resistance, decreased solubility and improved dimensional stability or resistance to creep under load to the resulting compositions and devices. Benefits associated with the use of polyisobutylene-based polymers include biostability and biocompatibility.

These and other aspects and embodiments as well as various additional advantages of the present invention will become readily apparent to those of ordinary skill in the art upon review of the Detailed Description and any Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to one aspect, the invention pertains to compositions comprising crosslinkable polyisobutylene homopolymers or copolymers (collectively referred to herein as "crosslinkable polyisobutylene polymers").

As is well known, "polymers" are molecules containing multiple copies (e.g., from 5 to 10 to 25 to 50 to 100 to 250 to 500 to 1000 or more copies) of one or more constitutional units, commonly referred to as monomers. As used herein, the term "monomers" may refer to free monomers and to those that have been incorporated into polymers, with the distinction being clear from the context in which the term is used.

Polymers may take on a number of configurations, which may be selected, for example, from linear, cyclic and branched configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyper branched polymers), and so forth.

As used herein, "homopolymers" are polymers that contain multiple copies of a single constitutional unit (i.e., monomer). "Copolymers" are polymers that contain multiple copies of at least two dissimilar constitutional units.

As used herein, a "polymer segment" or "segment" is a portion of a polymer. Polymer segments can be unbranched or branched. Polymer segments can contain a single type of constitutional unit (also referred to herein as "homopolymers segments") or multiple types of constitutional units (also referred to herein as "copolymer segments") which may be present, for example, in a random, statistical, gradient, or periodic (e.g., alternating) distribution.

As used herein a soft segment is one that displays a Tg that is below body temperature, more typically from 35° C. to 20° C. to 0° C. to −25° C. to −50° C. or below. A hard segment is one that displays a Tg that is above body temperature, more typically from 40° C. to 50° C. to 75° C. to 100° C. or above. Tg can be measured by differential scanning calorimetric (DSC), dynamic mechanical analysis (DMA) and thermo mechanical analysis (TMA).

As noted above, in one aspect, the invention pertains to crosslinkable compositions comprising crosslinkable polyisobutylene polymers. Polyisobutylene polymers may be rendered crosslinkable, for example, by providing at least one reactive group within the polymer, for instance, at least one site of carbon-carbon unsaturation (e.g., corresponding to —CH═CH— or —C≡C—) within the polymer, and more typically two or more sites of carbon-carbon unsaturation (e.g., 2, 3, 4, 5, 10 or more), among other possibilities. As a general rule, the greater the number of reactive groups (e.g., carbon-carbon unsaturation sites, etc.) in the polymer, the greater the crosslinking density in the final product.

For example, in certain embodiments, polyisobutylene homopolymers of the following formula (I) may be formed, which have terminal double bonds (i.e., vinyl groups):

(I)

where n is an integer of 2 or more (for example, ranging from 2 to 5 to 10 to 25 to 50 to 100 to 250 to 500 to 1000 to 3,000, among other values). Polyisobutylene copolymers that comprise one or more polyisobutylene segments, one or more non-polyisobutylene segments (several examples of which are described below), and terminal vinyl groups may also be formed for use in the present invention.

Although the preceding polyisobutylene polymers have terminal double bonds, in other embodiments, polyisobutylene homopolymers and copolymers having non-terminal double bonds are employed in the practice of the invention. Examples include polymer of the following formula (II), which have internal double bonds:

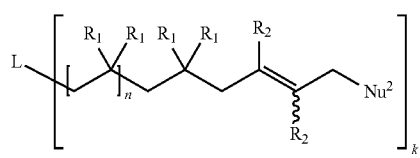
(II)

where n is an integer of 2 or more (for example, ranging from 2 to 5 to 10 to 25 to 50 to 100 to 250 to 500 to 1000 to 3,000, among other values); k is an integer of 1, 2, 3, 4, 5 or more, L is an initiator residue, $R_1$ is —$CH_3$, $R_2$ for each occurrence is independently —H, —X, —$CH_2X$, $CHX_2$, —$CX_3$, —C≡N or —$NO_2$, wherein X, for each occurrence, is independently a halogen; $Nu^2$ is selected from —OH, —$NH_2$, halogen, —$N_3$, —O—$CH_2C_2H$, —$OR_3$ (wherein $R_3$ is a C1-C12 alkyl), a polymer or copolymer segment, thymine, —$CH_2$—C(O)OH, —C(O)$N_3$, —NHC(O)OR, —C(O)NHR, or —NHC(O)NHR, where R is a C1-C12 alkyl, or a peptide-NH— group. See, e.g., WO 2008/060333 to Faust. In certain embodiments, $Nu^2R_3$ in formula (II) is a non-polyisobutylene polymer segment such as those described below.

Polyisobutylene homopolymers and copolymers of the formula (II) may be used per se in the compositions of the invention, or they may be used to form further copolymers for use in the invention as discussed in more detail below, for example, polyisobutylene urethane copolymers (e.g., where Nu2 is —OH), polyisobutylene urea copolymers (e.g., where Nu2 is —$NH_2$) or polyisobutylene urethane/urea copolymers (e.g., where Nu2 is —OH, —$NH_2$, or a combination of both) may be formed. Urethane, urea and urethane/urea copolymers can also be formed using isocyanate terminated polyisobutylene (i.e., where Nu2 is replaced with —N═C═O).

Polyurethanes are a family of copolymers that are typically synthesized from polyfunctional isocyanates (e.g., diisocyanates, including both aliphatic and aromatic diisocyanates) and polyols (e.g., macroglycols). For example, polyurethanes in accordance with the invention may be synthesized from a macroglycol (e.g., a macrodiol) that contains one or more polyisobutylene segments and one or more optional non-polyisobutylene segments. Aliphatic or aromatic diols and/or diamines may also be employed as chain extenders, for example, to impart improved physical properties to the polyurethane. For instance, hardness (Durometer) may be increased as a result of an increase the ratio of hard segments (e.g., arising from aromatic diisocyantes such as MDI, etc.) to soft segments in the copolymer through the use of chain extenders. Where diamines are employed as chain extenders, urea linkages are formed and the resulting polymers may be referred to as polyurethane/polyureas.

Polyureas are a family of copolymers that are typically synthesized from polyfunctional isocyanates and polyamines. For example, polyureas in accordance with the invention may be synthesized from a diamine that contains one or more polyisobutylene segments and one or more optional non-polyisobutylene segments. As with polyurethanes, aliphatic or aromatic diols or diamines may be employed as chain extenders.

Note that analogous urethane, urea and urethane/urea copolymers can be formed by reversing the species upon which the isocyanates, alcohol and amine functionalities are provided, for example, using macromolecular polyfunctional isocyanates to provide soft segments (e.g., a polyisobutylene-containing diisocyante, for instance, polymers of the formula (II) where Nu is —C≡N), small molecule diols or diamines to provide hard segments (e.g., aromatic diols or diamines, for instance, methylenebisphenylene diol) and small molecule diisocyanates as chain extenders.

As noted above, urethane, urea and urethane/urea copolymers in accordance with the invention typically comprise one or more one or more sites of unsaturation. For example, according to certain aspects of the invention, polyisobutylene urethane, urea and urethane/urea copolymers are provided, which contain (a) one or more polyisobutylene segments, (b) one or more one or more sites of unsaturation (c) one or more diisocyanate residues, (d) one or more optional chain extender residues and (e) one or more optional non-polyisobutylene polymer segments.

The one or more sites of unsaturation may be introduced into the urethane, urea and urethane/urea copolymers of the invention in various ways. For example, in certain embodiments of the invention, the unsaturated copolymers in accordance with the invention may be formed using one or more of the following species: (a) macroglycols (e.g., macrodiol) containing one or more sites of unsaturation (e.g., an unsaturated macroglycol containing one or more polyisobutylene segments, an unsaturated macroglycol containing one or more non-polyisobutylene polymer segments, or an unsaturated macroglycol containing one or more polyisobutylene segments and one or more non-polyisobutylene polymer segments), (b) diisocyanates containing one or more sites of unsaturation and (c) chain extender residues containing one or more one or more sites of unsaturation.

Examples of optional non-polyisobutylene segments include soft and hard polymer segments such as polyether segments, fluoropolymer segments including fluorinated polyether segments, polyester segments, poly(acrylate) segments, poly(methacrylate) segments, polysiloxane segments, polystyrene segments, and polycarbonate segments. As noted above, in certain embodiments, such non-polyisobutylene segments are introduced into the copolymers of the invention in the form of macroglycols (e.g., diols). Moreover, in certain embodiments, such non-polyisobutylene segments may be provided with one or more sites of unsaturation.

Examples of polyether segments include linear, branched and cyclic homopoly(alkylene oxide) and copoly(alkylene oxide) segments, including homopolymers and copolymer segments formed from one or more of the following, among others: methylene oxide, dimethylene oxide (ethylene oxide), trimethylene oxide, propylene oxide, and tetramethylene oxide, pentamethylene oxide, and hexamethylene oxide and higher analogs.

In this regard, in some embodiments, a polyether diol compatibilizer such as polytetramethylene oxide diol (PTMO diol) or polyhexameytheylene oxide diol (PHMO diol) may be added to a unsaturated polyisobutylene homopolymers diol during synthesis process in order to promote uniform distribution of the polyurethane hard segments into the PIB soft segments and to achieve favorable micro-phase separation in the polymer. Such polyalkylene oxides will also improve key mechanical properties such as one or more of the following: tensile strength, tensile modulus, flexural modulus, elongation, tear strength, flex fatigue, tensile creep, and abrasion performance, among others. The soft segment composition in the reaction mixture can be varied by varying the weight ratio of PIB diol to polyether diol (e.g., PTMO diol, PHMO diol, etc.) from, for example, 100:0, 99:1 to 95:5 to 90:10 to 75:25 to 50:50 to 25:75 to 10:90 to 5:95 to 0.1:99.9, more preferably, from 90:10 to 85:15 to 80:20 to 75:25 to 70:30. The PIB diol, polyether diol or both may be provided with one or more sites of unsaturation in some embodiments.

Similarly, the weight ratio of soft segment (e.g., polyisobutylene segment and non-polyisobutylene soft segment, if any) to hard segment (e.g., aromatic diisocyanate with chain extender, e.g. butanediol) in the polyurethanes of the invention can be varied, for example, from 99:1 to 95:5 to 90:10 to 75:25 to 50:50 to 25:75 to 10:90 to 5:95 to 1:99, more preferably, 95:5 to 90:10 to 80:20 to 70:30 to 65:35 to 60:40 to 50:50, to achieve a variety of Shore hardness, a wide range of physical and mechanical properties, and an array of functional performance.

Examples of soft fluoropolymer segments include perfluoroacrylate segments and fluorinated polyether segments, for example, linear, branched and cyclic homopoly(fluorinated alkylene oxide) and copoly(fluorinated alkylene oxide) segments, including homopolymeric and copolymer segments formed from one or more of the following, among others: perfluoromethylene oxide, perfluorodimethylene oxide (perfluoroethylene oxide), perfluorotrimethylene oxide and perfluoropropylene oxide.

Examples of soft polyester segments include linear, branched and cyclic homopolymeric and copolymer segments formed from one or more of the following, among others: alkyleneadipates including ethyleneadipate, propyleneadipate, tetramethyleneadipate, and hexamethyleneadipate.

Examples of soft poly(acrylate) segments include linear, branched and cyclic homopoly(acrylate) and copoly(acrylate) segments, including homopolymeric and copolymer segments formed from one or more of the following, among others: alkyl acrylates such as methyl acrylate, ethyl acrylate, propyl acrylate, isopropyl acrylate, butyl acrylate, sec-butyl acrylate, isobutyl acrylate, 2-ethylhexyl acrylate and dodecyl acrylate.

Examples of soft poly(methacrylate) segments include linear, branched and cyclic homopoly(methacrylate) and copoly(methacrylate) segments, including homopolymeric and copolymer segments formed from one or more of the following, among others: alkyl methacrylates such as hexyl methacrylate, 2-ethylhexyl methacrylate, octyl methacrylate, dodecyl methacrylate and octadecyl methacrylate.

Examples of soft polysiloxane segments include linear, branched and cyclic homopolysiloxane and copolysiloxane segments, including homopolymeric and copolymer segments formed from one or more of the following, among others: dialkyl siloxanes such as dimethyl siloxane, diethyl siloxane, and methylethyl siloxane.

Examples of soft polycarbonate segments include those comprising one or more types of carbonate units,

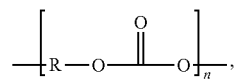

where R may be selected from linear, branched and cyclic alkyl groups. Specific examples include homopolymeric and copolymer segments formed from one or more of the following monomers, among others: ethylene carbonate, propylene carbonate, and hexamethylene carbonate.

As indicated above, examples of optional non-polyisobutylene segments also include hard polymer segments such as poly(vinyl aromatic) segments, poly(alkyl acrylate) and poly(alkyl methacrylate) segments.

Examples of hard poly(vinyl aromatic) segments include linear, branched and cyclic homopoly(vinyl aromatic) and copoly(vinyl aromatic) segments, including homopolymeric and copolymer segments formed from one or more of the following vinyl aromatic monomers, among others: styrene, 2-vinyl naphthalene, alpha-methyl styrene, p-methoxystyrene, p-acetoxystyrene, 2-methylstyrene, 3-methylstyrene and 4-methylstyrene.

Examples of hard poly(alkyl acrylate) segments include linear, branched and cyclic homopoly(alkyl acrylate) and copoly(alkyl acrylate) segments, including homopolymeric and copolymer segments formed from one or more of the following acrylate monomers, among others: tert-butyl acrylate, hexyl acrylate and isobornyl acrylate.

Examples of hard poly(alkyl methacrylate) segments include linear, branched and cyclic homopoly(alkyl methacrylate) and copoly(alkyl methacrylate) segments, including homopolymeric and copolymer segments formed from one or more of the following alkyl methacrylate monomers, among others: methyl methacrylate, ethyl methacrylate, isopropyl methacrylate, isobutyl methacrylate, t-butyl methacrylate, and cyclohexyl methacrylate.

Examples of optional non-polyisobutylene segments further include biodegradable linear, branched and cyclic homopolymeric and copolymer segments, for example, formed from one or more of the following, among others: d-lactic acid, 1-lactic acid, glycolic acid, epsilon caprolactone, and d,l-lactic acid, hydroxybutyrates, tyrosine polyesters, tyrosine polycarbonates, polyesteramides, and polyanhydrides.

The various polyisobutylene and optional non-polyisobutylene polymer segments described herein can vary widely in molecular weight, but typically are composed of between 2 and 1000 repeat units (monomer units), for example, ranging from 2 to 5 to 10 to 25 to 50 to 100 to 250 to 500 to 1000 repeat units.

As noted above, the various polyisobutylene and optional non-polyisobutylene polymer segments described herein may be provided with one or more reactive groups (e.g., one or more sites of unsaturation) in some embodiments.

The various polyisobutylene and optional non-polyisobutylene polymer segments described herein can be incorporated into the polyurethanes, polyureas and polyurethane/ polyureas of the invention by providing them in the form of polyols (e.g., diols, triols, etc.) or as polyamines (e.g., diamines, triamines, etc.). Although polyols are generally described herein, it is to be understood that analogous methods may be performed and analogous compositions may be created using polyamines and polyol/polyamine combinations.

Specific examples of polyisobutylene polyols include linear polyisobutylene diols and branched polyisobutylene polyols (e.g., three-arm polyisobutylene triols) which may contain two or more sites of unsaturation or which may be saturated (e.g., where unsaturation is introduced via another entity). See, e.g., WO 2008/060333 to Faust, J. P. Kennedy et al., "Designed Polymers by Carbocationic Macromolecular Engineering: Theory and Practice," Hanser Publishers 1991, pp. 191-193, Joseph P. Kennedy, Journal of Elastomers and Plastics 1985 17: 82-88, and the references cited therein. More specific examples include linear polyisobutylene diols with a terminal —OH functional group at each end and with zero, one, two, three or more sites of unsaturation, which may be formed, for example, using methods analogous to those described in the preceding Faust and Kennedy references.

Specific examples of polyether polyols include polytetramethylene oxide diols, which are available from various sources including Signa-Aldrich Co., Saint Louis, Mo., USA and E.I. duPont de Nemours and Co., Wilmington, Del., USA. Specific examples of polysiloxane polyols include polydimethylsiloxane diols, available from various sources including Dow Corning Corp., Midland Mich., USA, Chisso Corp., Tokyo, Japan. Specific examples of polycarbonate polyols include polyhexamethylene carbonate diols such as those available from Sigma-Aldrich Co. Specific examples of polyfluoroalkylene oxide diols include ZDOLTX, Ausimont, Bussi, Italy, a copolyperfluoroalkylene oxide diol containing a random distribution of —CF2CF2O— and —CF2O— units, end-capped by ethoxylated units, i.e., H(OCH2CH2) nOCH2CF2O(CF2CF2O)p(CF2O)qCF2CH2O(CH2CH2O) nH, where n, p and q are integers. Polystyrene diol (α,ω-dihydroxy-terminated polystyrene) of varying molecular weight is available from Polymer Source, Inc., Montreal, Canada. Polystyrene diols and three-arm triols may be formed, for example, using procedures analogous to those described in M. Weißmüller et al., "Preparation and end-linking of hydroxyl-terminated polystyrene star macromolecules," Macromolecular Chemistry and Physics 200(3), 1999, 541-551.

In some embodiments, polyols (e.g., diols, triols, etc.) are employed which are based on block copolymers. Specific examples of such block copolymer polyols include the following (which may contain zero, one, two or more sites of unsaturation): poly(tetramethylene oxide-b-isobutylene) diol, poly(tetramethylene oxide-b-isobutylene-b-alkylene oxide)diol, poly(dimethyl siloxane-b-isobutylene)diol, poly (dimethyl siloxane-b-isobutylene-b-dimethyl siloxane)diol, poly(hexamethylene carbonate-b-isobutylene)diol, poly (hexamethylene carbonate-b-isobutylene-b-hexamethylene carbonate)diol, poly(methyl methacrylate-b-isobutylene) diol, poly(methyl methacrylate-b-isobutylene-b-methyl methacrylate)diol, poly(styrene-b-isobutylene)diol and poly (styrene-b-isobutylene-b-styrene)diol (SIBS diol).

Specific examples of homopolymeric and copolymeric polyisobutylene polyols (and polyamines) which may be used in forming the polyisobutylene urethane, urea and urethane/urea copolymers of the invention include polymers of formula (II)

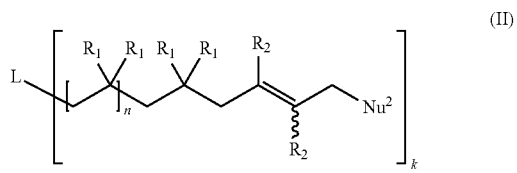

where n is an integer of or more 2 (for example, ranging from 2 to 5 to 10 to 25 to 50 to 100 to 250 to 500 to 1000 to 3000, among other values); k is an integer of 1, 2, 3, 4, 5 or more, L is an initiator residue, $R_1$ is —$CH_3$, $R_2$ for each occasion is independently —H, —X, —$CH_2X$, $CHX_2$, —$CX_3$, —C≡N or —$NO_2$, wherein X, for each occurrence, is independently a halogen (preferably $R_2$ is —H); and $Nu^2$ is selected from —OH, —$NH_2$, or —$OR_3$, wherein $R_3$ is a non-polyisobutylene segment such as those described above with —OH or —$NH_2$ termination.

As noted above, polyisobutylene urethane, urea and urethane/urea copolymers in accordance with the invention typically comprise one or more diisocyanate residues and will also comprise one or more chain extender residues in many embodiments.

Diisocyanates for use in forming the urethane, urea and urethane/urea copolymers of the invention include aromatic and non-aromatic (e.g., aliphatic) diisocyanates. Aromatic diisocyanates may be selected from suitable members of the following, among others: 4,4'-methylenediphenyl diisocyanate (MDI), 2,4- and/or 2,6-toluene diisocyanate (TDI), 1,5-naphthalene diisocyanate (NDI), para-phenylene diisocyanate, 3,3'-tolidene-4,4'-diisocyanate and 3,3'-dimethyl-diphenylmethane-4,4'-diisocyanate. Non-aromatic diisocyanates may be selected from suitable members of the following, among others: 1,6-hexamethylene diisocyanate (HDI), 4,4'-dicyclohexylmethane diisocyanate, 3-isocyanatomethyl-3,5,5-trimethylcyclohexyl isocyanate (isophorone diisocyanate or IPDI), cyclohexyl diisocyanate, and 2,2,4-trimethyl-1,6-hexamethylene diisocyanate (TMDI). In embodiments where diisocyanates which contain one or more one or more sites of unsaturation are employed, examples of such diisocyanates include for example those materials described in U.S. Pat. No. 3,505,252 to Brotherton et al., among others.

Optional chain extenders are typically aliphatic or aromatic diols (in which case a urethane bond is formed upon reaction with an isocyanate group) or aliphatic or aromatic diamines (in which case a urea bond is formed upon reaction with an isocyanate group). Chain extenders may be selected from suitable members of the following, among others: alpha, omega-alkane diols such as ethylene glycol (1,2-ethane diol), 1,4-butanediol, 1,6-hexanediol, alpha,omega-alkane diamines, such as ethane diamine, dibutylamine(1,4-butane diamine) and 1,6-hexanediamine, or 4,4'-methylene bis(2-chloroaniline). In embodiments where chain extenders containing one or more one or more sites of unsaturation are employed, examples of such chain extenders include the preceding diols with one or more one or more sites of unsaturation, for example, alpha,omega-alkene diols such as 1,2-ethene diol, 1,4-butenediol, 1,6-hexenediol, and so forth, or alpha,omega-alkene diamines such as 1,2-ethene diamine, 1,4-butene diamine, 1,6-hexene diamine, and so forth Chain extenders may be also selected from suitable members of the following, among others: short chain diol polymers (e.g., alpha,omega-dihydroxy-terminated polymers having a number average molecular weight less than or equal to 1000) based on hard or soft polymer polyisobutylene and non-polyisobutylene segments such as those described above (more typically soft polymer segments), including short chain polyisobutylene diols, short chain polyether polyols such as polytetramethylene oxide diols, short chain polysiloxane diols such as polydimethylsiloxane diols, short chain polycarbonate diols such as polyhexamethylene carbonate diols, short chain poly(fluorinated ether)diols, short chain polyester diols, short chain polyacrylate diols, short chain polymethacrylate diols, and short chain poly(vinyl aromatic)diols. In certain embodiments, such short chain diol polymers may have one or more one or more sites of unsaturation.

As is known in the polyurethane art, chain extenders can increase the hard segment content in the urethane, urea or urethane/urea polymer (or, stated another way, can increase the ratio of hard segment material to soft segment material in the polymer), which can in turn result in a polymer with higher modulus, lower elongation at break and increased strength. Such chain extenders may also be used to supply sites of unsaturation within the polymers of the present invention as noted above.

Polyisobutylene urethane, urea and urethane/urea copolymers in accordance with the invention may the synthesized, for example, in bulk or using a suitable solvent (e.g., one capable or dissolving the various species that participate in the polymerization reaction). In certain embodiments, polyisobutylene urethane, urea and urethane/urea copolymers in accordance with the invention are synthesized via reactive extrusion.

Various synthetic strategies may be employed to create polyisobutylene urethane, urea and urethane/urea polymers in accordance with the invention. These strategies typically involved the reaction of (a) one or more polyol (commonly diol) species and one or more polyisocyanate (commonly diisocyanate) species, (b) one or more polyamine (commonly diamine) species and one or more polyisocyanate species, or (c) one or more polyol species, one or more polyamine species and one or more polyisocyanate species. Reaction may be conducted, for example, neat, in organic solvents, or using supercritical $CO_2$ as a solvent. Ionomers can be used for polymer precipitation.

For example, in certain embodiments, a one step method may be employed in which a first macrodiol (M1) (e.g., a polyisobutylene diol with two or more sites of unsaturation, etc.) and a diisocyante (DI) (e.g., MDI, TDI, etc.) are reacted in a single step. Molar ratio of diisocyanate relative to the first macrodiol is 1:1. Using this technique a polyurethane having alternating macrodiol and diisocyante residues, i.e., -[DI-M1-]$_n$, where n is an integer, may be formed. In some embodiments, a diol or diamine chain extender (CE) (e.g., 1,2-ethane diol, 1,4-butanediol, 1,6-hexanediol, etc., or a diol with one or more sites of unsaturation) is included in the reaction mixture, in which case the molar ratio of diisocyanate relative to the combination of the first macrodiol and the chain extender is 1:1. For example, the ratio DI:M1:CE may equal 2:1:1, may equal 2:1.5:0.5, may equal 2:0.5:1.5, among many other possibilities. Where a ratio of DI:M1:CE equal to 2:1:1 is employed, a polyurethane having the following structure may be formed -[DI-M1-DI-CE-]$_n$. Reactions of this type have been reported to follow a statistical distribution, so M1 and CE residues are not likely to be perfectly alternating as shown. See, e.g., F. Wang, "Polydimethylsiloxane Modification of Segmented Thermoplastic Polyurethanes and Polyureas, Ph.D. dissertation, Virginia Polytechnic Institute and State University, Apr. 13, 1998.

In other embodiments, a two-step reaction is employed wherein the first macrodiol and diisocyante are reacted in a single step at a DI:M1 molar ratio of ≥2:1 in order to form isocyanate-end-capped "prepolymers," DI-M1-DI. Then, in a second step, a chain extender is added, along with additional diisocyanate, if required to maintain an overall molar ratio of diisocyanate relative to the combination of the first macrodiol and the chain extender of 1:1. As above, where a molar ratio of DI:M1:CE equal to 2:1:1 is employed, a polyurethane having the following structure may be formed -[DI-M1-DI-CE-]$_n$, although the Ml and CE residues may not be perfectly alternating as shown. Due to enhanced reaction control, polyurethanes made by the two-step method tend to have a more regular structure than corresponding polyurethanes made by the one step method.

In certain other embodiments, a one step method may be employed in which a first macrodiol (M1) (e.g., a polyisobutylene diol with zero, one, two or more sites of unsaturation, etc.), a second macrodiol (M2) (e.g., a polyether diol, a fluoropolymer diol, a polysiloxane diol, a polycarbonate diol, a polyester diol, a polyacrylate diol, a polymethacrylate diol, a polystyrene diol, etc. with zero, one, two or more sites of unsaturation) and a diisocyante (DI) (e.g., MDI, TDI, etc.) are reacted in a single step. Molar ratio of diisocyanate relative to the first and second diols is 1:1. For example, the ratio DI:M1:M2 may equal 2:1:1, may equal 2:1.5:0.5, may equal 2:0.5:1.5, among many other possibilities. Where a ratio of DI:M1:M2 equal to 2:1:1 is employed, a polyurethane having the following structure may be formed -[DI-M1-DI-M2-]$_n$ although the chains are unlikely to be perfectly alternating as shown. In some embodiments, a chain extender is added to the reaction mixture, such that the molar ratio of diisocyanate relative to the first and second macrodiols and chain extender is 1:1. For example, the ratio DI:M1:M2:CE may equal 4:1:1:2, may equal 2:0.67:0.33:1, may equal 2:0.33:0.67:1, or may equal 5:1:1:3, among many other possibilities. Where a ratio of DI:M1:M2:CE equal to 4:1:1:2 is employed, a polyurethane having the following structure may be formed -[DI-M1-DI-CE-DI-M2-DI-CE-]$_n$, although the chains are unlikely to be perfectly alternating as shown.

In some embodiments, a two-step method is employed in which first and second macrodiols and diisocyante are reacted in a ratio of DI:M1:M2 of ≥2:1:1 in a first step to form isocyanate capped first and second macrodiols, for example DI-M1-DI and DI-M2-DI. In a second step, a chain extender is added which reacts with the isocyanate end caps of the macrodiols. In some embodiments, the number of moles of hydroxyl or amine groups of the chain extender may exceed the number of moles of isocyanate end caps for the macrodiols, in which case additional diisocyante may be added in the second step as needed to maintain a suitable overall stoichiometry. As above, the molar ratio of diisocyanate relative to the total of the first macrodiol, second macrodiol, and chain extender is typically 1:1, for example, DI:M1:M2:CE may equal 4:1:1:2, which may in theory yield an idealized polyurethane having the following repeat structure -[DI-M1-DI-CE-DI-M2-DI-CE-]$_n$, although the chains are unlikely to be perfectly alternating as shown. In other examples, the DI:M1:M2:CE ratio may equal 4:1.5:0.5:2 or may equal 5:1:1:3, among many other possibilities.

In some embodiments, three, four or more steps may be employed in which a first macrodiol and diisocyante are reacted in a first step to form isocyanate capped first macrodiol, typically in a DI:M1 ratio of ≥2:1 such that isocyanate end caps are formed at each end of the first macrodiol (although other ratios are possible including a DI:M1 ratio of 1:1, which would yield an average of one isocyanate end caps per macrodiol). This step is followed by second step in which the second macrodiol is added such that it reacts with one or both isocyanate end caps of the isocyanate capped first macrodiol. Depending on the relative ratios of D1, M1 and M2, this step may be used to create structures (among other statistical possibilities) such as M2-DI-M1-DI-M2 (for a DI:M1:M2 ratio of 2:1:2), M2-DI-M1-DI (for a DI:M1:M2 ratio of 2:1:1), or M1-DI-M2 (for a DI:M1:M2 ratio of 1:1:1).

In certain embodiments, a mixed macrodiol prepolymer, such as one of those in the prior paragraph, among others (e.g., M2-DI-M1-DI-M2, M1-DI-M2-DI-M1, DI-M1-DI-M2, etc.) is reacted simultaneously with a diol or diamine chain extender and a diisocyanate, as needed to maintain stoichiometry. For example, the chain extension process may be used to create idealized structures along the following lines, among others: -[DI-M2-DI-M1-DI-M2-DI-CE-]$_n$, -[DI-M1-DI-M2-DI-M1-DI-CE-]$_n$ or [-DI-M1-DI-M2-DI-CE-]$_n$, although it is again noted that the chains are not likely to be perfectly alternating as shown. In certain other embodiments, a mixed macrodiol prepolymer is reacted with sufficient diisocyanate to form isocyanate end caps for the mixed macrodiol prepolymer (e.g., yielding DI-M2-DI-M1-DI-M2-DI, DI-M1-DI-M2-DI-M1-DI or DI-M1-DI-M2-DI, among other possibilities). This isocyanate-end-capped mixed macrodiol can then be reacted with a diol or diamine chain extender (and a diisocyanate, as needed to maintain stoichiometry). For example, the isocyanate-end-capped mixed macrodiol can be reacted with an equimolar amount of a chain extender to yield idealized structures of the following formulae, among others: -[DI-M2-DI-M1-DI-M2-DI-CE-]$_n$, -[DI-M1-DI-M2-DI-M1-DI-CE-]$_n$ or -[DI-M1-DI-M2-DI-CE-]$_n$.

Using the above and other techniques, a wide variety of crosslinkable polyisobutylene polymers, including various urethanes, ureas and urethane/ureas can be formed. Typical number average molecular weights for the crosslinkable polyisobutylene polymers within the crosslinkable compositions of the invention range from 1,000 to 300,000 daltons, among other values, for instance, ranging from 1,000 to 2,000 to 5,000 to 10,000 to 15,000 to 20,000 to 25,000 to 50,000 to 100,000 to 300,000 Daltons. Durometer values, which are influenced, for example, by the type of diisocyanate and by the ratio of hard segments to soft segments in the polymer (which is in turn influenced, for example, by the length of the soft segments in the polymer and the degree of chain extension, if any), can vary widely, and typically ranges from 10 A to 75 D, for instance, range from 10 A to 20 A to 30 A to 40 A to 50 A to 60 A to 70 A to 80 A to 90 A to 100 A (=58 D) to 60 D to 65 D to 70 D to 75 D.

In various aspects of the invention, crosslinkable compositions are provided, which comprise (a) one or more types of crosslinkable polyisobutylene polymers and (b) one or more optional supplemental agents such as (i) therapeutic agents (numerous examples of which are described below) and (ii) chemical agents that promote crosslinking ("crosslinking agents") such as catalysts, initiators including photoinitiators, redox initiators and heat labile initiators, accelerators, hardening agents, and additional unsaturated polymers, and so forth and (iii) fluoroscopy markers, among others.

Crosslinking may progress with the aid of suitable crosslinking species, for example, species that aid in completion of a chemical reaction without becoming part of the reaction product (e.g., catalysts, accelerators, etc.) and/or species that become part of the crosslinked polymer network (e.g., initiators, hardening agents, additional monomers, polymers, etc.), among others.

Crosslinking may be initiated by exposure to energy (e.g., the application of heat or ionizing or non-ionizing radiation such as e-beam radiation, gamma radiation, UV light, etc.), a chemical agent (e.g., moisture, a hardening agent, etc.), or both.

Examples of initiators include free-radical generating species, which may be activated or accelerated by the application of heat (i.e., thermal initiators, such as peroxide initiators, azo initiators, etc.) and/or light (i.e., photoinitiators, such as benzoin ethers, aryl ketones, acyl phosphine oxides, etc.).

Examples of peroxide initiators for thermal initiation include the following: benzoyl peroxide, t-amyl peracetate, 2,5-dimethyl-2,5-bis(t-butylperoxy)-3-hexyne, 2,5-dimethyl-2,5-di-(t-butylperoxy)-hexane, t-butyl alpha-cumyl peroxide, di-butyl peroxide, t-butyl hydroperoxide, dichlorobenzoyl peroxide, dicumyl peroxide, di-t-butyl peroxide, 2,5 dimethyl-2,5-di(peroxy benzoate)-3-hexyne, 1,3-bis(t-butyl peroxy isopropyl)benzene, lauroyl peroxide, di-t-amyl peroxide, 1,1-di-(t-butylperoxy)cyclohexane, 2,2-di-(t-butylperoxy) butane, and 2,2-di-(t-amylperoxy) propane.

Azo compounds such as 2,2'-azobisisobutyronitrile (AIBN) and V-50 and V-086 from Wako Specialty Chemicals, or AZDN, AIVN, and Azocarboxy from Arkema, among others, may also be employed for thermal initiation.

Specific examples of photoinitiators include benzoin ether, benzil dimethyl ketone acetal, 1-hydroxycyclohexyl phenyl ketone, 2-hydroxy-2-methyl-1-phenyl-propane-1-one, diethoxyacetophenone, benzophenone, methylthioxanone, 2,4,6,trimethylbenzoyl diphenyl phosphine oxide (TPO), acyl phosphine oxide (APO) and bis acyl phosphine oxide (BAPO).

Without wishing to be bound by theory, it is believed that a free radical initiator forms a radical, which attacks a carbon-carbon double bond within another entity (e.g., a carbon-carbon double bond with a crosslinkable polyisobutylene polymer of the invention) forming a radical in that entity. Once formed, a radical on one entity may, for example, attack a double bond in another entity (e.g., in another crosslinkable polymer) forming a chemical bond between the entities and a new radical center. Alternatively, radicals on two different entities may combine to form a bond between the entities without the creation of a new radical center (a process called combination). Regardless of the precise reaction mechanism, crosslinks are created between the entities. The resulting crosslinks are based on the formation of carbon-carbon bonds, without the formation of functional groups (e.g., ester, amide, etc.) that are prone to hydrolysis and other forms of degradation.

Crosslinking may be enhanced when the polymer is in a mobile state, for example, in a melt state, which state may be established concurrently with radical formation, or subsequent to radical formation.

Free radical crosslinking reactions may also be promoted by the introduction of multifunctional crosslinking agents having two or more sites of unsaturation (e.g., —HC=CH—, —HC=CH$_2$, —C≡C— or —C≡CH). For example, in some embodiments of the invention, vinyl crosslinking agents may be added to enhance crosslinking between the polymers. For instance, alkenes such as HC=CH—(CH$_2$)$_n$—HC=CH or HC=CH—[CH$_2$—C(CH$_3$)$_2$]$_n$—HC=CH, where n is an integer, for example, ranging from 0 to 20, may be used for this purpose. Note that the latter species is a short (e.g., 20 monomers or less) terminally unsaturated polyisobutylene crosslinking agent. In this regard, compatibility between the crosslinking agents and the polymers of the invention may be enhanced by using multifunctional crosslinking agents that contain polymer blocks which have the same or similar monomer composition as is found in the polymer to be crosslinked. In other embodiments, short terminally unsaturated polymers corresponding to any additional blocks used within the polymers of the invention may be employed as crosslinking agents (e.g., short terminally unsaturated polyether segments, poly(acrylate) segments, poly(methacrylate) segments, polysiloxane segments, polycarbonate segments, etc.).

Additional examples of multifunctional crosslinking agents include polymers containing unsaturation along the backbone, for example, poly(butadiene), which can crosslink with the polyisobutylene urethane, urea or urethane/urea copolymer, and unsaturated monomers that can polymerize during the crosslinking reaction. These monomers may have functionality built in, for example, containing epoxide groups, carboxyl groups or hydroxyl groups, among others.

Other crosslinking strategies besides free-radical based crosslinking strategies may be employed in conjunction with the invention. For example, a peroxyacid, for instance, a peroxy-carboxylic acid such as meta-chloroperoxybenzoic acid (mCPBA), among others, may be used to oxidize carbon-carbon double bonds in the polymers of the invention to generate epoxide groups (oxiranes). The resulting epoxide-containing polymer may be crosslinked by exposure to radiation (either ionizing or non-ionizing). The resulting epoxide-containing polymer may also be crosslinked by exposure to a curing agent, for instance, a multifunctional amine such as triethylenetetramine (TETA) or difunctional amines such as are described below. When these are mixed together, the amine groups react with the epoxide groups to form a covalent bond.

As another example, crosslinking may be achieved by use of "click" chemistry. Typical reactions include reaction of terminal alkynes with azides, reaction of activated nitriles such as toluenesulfonyl cyanide with unhindered azides, or nucleophilic ring opening reactions of strained rings such as epoxides, aziridines or cyclic sulfates. The alkynes can be pendant groups at any location in the polyisobutylene urethane, urea or urethane/urea copolymer (collectively PIBPU), for example, in the PIB segments, or in the diisocyanate segments. In a typical crosslinking reaction, a PIB PU with pendant alkynes would be reacted with an aliphatic or aromatic diazide. Alternately, reaction of epoxide rings in the backbone of the PIB PU with diamines will result in crosslinking through ring opening polymerization.

As yet another example, crosslinking may be achieved by hydrosilation. Hydrosilation involves the addition of a Si—H bond across an unsaturated carbon-carbon bond. This addition is catalyzed by noble metals, typically platinum. An example of a crosslinking agent useful for this purpose is a multifunctional silicon hydride.

As another example, crosslinking may be achieved by first hydrosilylating unsaturated polymers such as those described herein with a silane compound, whereupon the silicon hydride bond (Si—H) reacts with the pendant olefinic unsaturation found in the polymer. As above, this reaction may be catalyzed by noble metals, typically platinum. The silane also contains one or more alklysiloxy groups for subsequent crosslinking reactions in this embodiment. An example of such a compound is tris(trimethylsiloxy)silane available from Sigma-Aldrich. Other examples include species of the formula $SiH_n(OR)_{4-n}$, where n is an integer of 1, 2 or 3 and R is selected from branched and unbanked alkyl groups having 1 to 10 carbon atoms and aryl groups having 6 to 10 carbon atoms. Such polymers are moisture curable (crosslinkable). In particular, crosslinking may proceed upon exposure to water, which causes the alkoxy groups in the polymer to be hydrolyzed, followed by condensation of neighboring hydroxyl groups to form the crosslinks containing —Si—O—Si— linkages. This process may be promoted, for example, by steam autoclaving or through the use of a suitable catalyst, for example an organo-tin catalyst.

In other embodiments, crosslinking may be achieved using polymers with terminal groups such as glycidyl or carboxylic acid groups. In such cases, the resultant crosslinked adhesive materials will be epoxides or esters and will be moisture cured in the presence or absence of heat.

As seen from the above, in certain embodiments, compositions in accordance with the invention may be crosslinked upon contact with a suitable multifunctional crosslinking agent such as a multifunctional amine, multifunctional epoxide, or a multifunctional silicon hydride, among others. In those embodiments, a composition comprising a crosslinkable polyisobutylene-based polymer in accordance with the invention may be provided in a first container and a multifunctional crosslinking agent (e.g., multifunctional amine, multifunctional silicon hydride, etc.) may be provided in a second container in the form of a kit.

In certain embodiments of the invention, crosslinkable compositions in accordance with the present invention are applied to one or more medical device components (e.g., as a coating on a medical device component or as an adhesive for attaching two or more medical device components) and then cured under suitable conditions (e.g., exposure to heat, radiation, multifunctional crosslinking agent, atmospheric moisture, etc.). Low molecular weight PIBPU with terminal double bonds and a free radical initiator is one of the several possibilities. Another possibility is PIBPU with terminal double bonds, a second low molecular weight polymer/oligomer with double bonds, and a free radical initiator.

Crosslinkable compositions in accordance with the present invention are particularly beneficial as coatings or adhesives for polyisobutylene containing polymers, for example, thermoplastic polyisobutylene copolymers such as those having one or more polyisobutylene segment and one or more hard segments. Examples of such copolymers include block copolymers having one or more polyisobutylene segment and one or more hard segment, for instance, selected from those described above (e.g., poly(vinyl aromatic), poly(alkyl acrylate) or poly(alkyl methacrylate) hard segments such as polystyrene, poly(tert-butyl acrylate) and poly(methyl methacrylate), among others. Specific examples of such polymers include triblock copolymers having a soft segment between two hard segments, for instance, poly(styrene-b-isobutylene-b-styrene), poly(tert-butyl acrylate-b-isobutylene-b-tert-butyl acrylate) and poly(methyl methacrylate-b-isobutylene-b-methyl methacrylate), among others.

Examples of such copolymers further include polyisobutylene containing polyurethanes, polyureas or polyurethane/polyureas, which may be prepared, for example, using techniques like those described above (except that the polyisobutylene, diisocyanate, and optional components such as chain extenders and non-polyisobutylene polymeric components need not contain one or more sites of unsaturation). Examples thus include polyurethanes, polyureas and polyurethane/polyureas having one or more polyisobutylene soft segments, one or more segments arising from aromatic diisocyanates (e.g., MDI, TDI, NDI, etc.), and one or more optional segments (e.g., segments arising from chain extenders and/or non-polyisobutylene polymer segments which may be selected, for instance, from those set forth above, among others).

As a specific example, crosslinkable compositions in accordance with the present invention may be used to coat or adhere one or more components, which one or more components contain a thermoplastic polyisobutylene urethane, urea or urethane/urea copolymer that comprises one or more polyisobutylene segments and one or more polytetramethylene oxide segments (e.g., a copolymer formed from polyisobutylene diol, polyhexamethylene oxide or polyhexamethylene oxide diol, MDI as a diisocyante and 1,4-butane diol as a chain extender, among other possibilities), for instance having a number average molecular weight of at least 1000 Daltons.

Where a crosslinkable composition of the invention is applied to a material comprising a non-polyisobutylene polymer segment (e.g., a polyether segment, polyacrylate segment, polymethacrylate segment, polyvinyl aromatic segment, polysiloxane segment, polycarbonate segment, etc.), in certain embodiments, the crosslinkable composition will contain a matching non-polyisobutylene entity (i.e., one with the same monomer content). For example, a matching non-polyisobutylene segment may be provided as a segment within the crosslinkable polyisobutylene polymer in the composition or it may be provided within a separate entity in the composition, for example, a crosslinking agent comprising such a non-polyisobutylene segment with terminal unsaturation may be included in the composition, among other possibilities. In a specific example, a polysiloxane segment (e.g., a polydimethylsiloxane segment) may be provided in the composition to enhance adhesion to silicone. Such a composition can be used, for example, to bond silicone to silicone or to bond silicone to a polyisobutylene-containing polymer.

In a specific example, crosslinkable compositions in accordance with the invention may comprise a low molecular weight polyisobutylene urethane, urea or urethane/urea copolymer (e.g., having a number average molecular weight ranging between 1000 and 50,000 Daltons, for instance ranging from 1,000 to 2,500 to 5,000 to 10,000 to 25,000 to 50,000 Daltons) which contains one or more polyisobutylene segments and two or more sites of unsaturation, along with any optional agents such as crosslinking agents, therapeutic agents and so forth (e.g., a composition comprising a copolymer formed from a divinyl or diallyl polyisobutylene diol, MDI as a diisocyanate and 1,4-butane diol as a chain extender and comprising as a crosslinking agent an organic peroxide (aromatic/aliphatic) such as dicumyl peroxide or benzoyl peroxide, a ketone such as benzophenone or methylphenyl ketone, an organic azide such as AIBN, or an organometallic catalyst such as a platinum complex).

As another specific example, crosslinkable compositions in accordance with the invention may comprise a low molecular weight polyisobutylene urethane, urea or urethane/urea copolymer (e.g., having a number average molecular weight ranging between 1,000 and 50,000 Daltons, for instance, ranging from 1,000 to 2,500 to 5,000 to 10,000 to 25,000 to 50,000 Daltons) which contains one or more polyisobutylene segments, one or more non-polyisobutylene polymer segments (e.g., one or more polytetramethylene oxide segments, etc.) and two or more sites of unsaturation, along with any optional agents such as crosslinking agents, therapeutic agents and so forth (e.g., a composition comprising a copolymer formed from a divinyl or diallyl polyisobutylene diol, polytetramethylene oxide diol, MDI as a diisocyanate and 1,4-butane diol as a chain extender and comprising as a crosslinking agent an organic peroxide (aromatic/aliphatic) such as dicumyl peroxide or benzoyl peroxide, an organic azide such as AIBN, or an organometallic catalyst such as a platinum complex).

As yet another specific example, crosslinkable compositions in accordance with the invention may comprise a low molecular weight polyisobutylene urethane, urea or urethane/urea copolymer (e.g., having a number average molecular weight ranging between 1,000 and 50,000 Daltons) which contains one or more polyisobutylene segments and two or more sites of unsaturation, a non-polyisobutylene-polymer-segment-containing crosslinking agent (e.g., a polytetramethylene oxide crosslinking agent having two or more sites of unsaturation), along with any optional agents such as crosslinking agents, therapeutic agents and so forth (e.g., a composition comprising (a) a copolymer formed from a divinyl or diallyl polyisobutylene diol, MDI as a diisocyante and 1,4-butane diol as a chain extender and (b) a crosslinking agent, for example, divinyl polytetramethylene oxide, an organic peroxide (aromatic/aliphatic) such as dicumyl peroxide or benzoyl peroxide, a ketone such as benzophenone or methylphenyl ketone, an organic azide such as AIBN and/or an organometallic catalyst such as a platinum complex, among others).

In certain embodiments, crosslinkable compositions in accordance with the present invention are used to form medical device components, for example, by molding or by reactive extrusion. For instance, in some embodiments, a crosslinkable composition in accordance with the present invention may be introduced into a mold and cured, for example, by heating or by exposure to radiation (e.g., using a mold that can be penetrated by the radiation of interest), or a crosslinkable composition in accordance with the present invention may be introduced into a mold along with a chemical species that leads to crosslinking (e.g., water/moisture, a multifunctional crosslinking agent, etc.) Such products will frequently have a seam or other evidence of having been molded, but not necessarily in every case.

In other embodiments, a crosslinkable composition in accordance with the present invention may be extruded in a reactive extrusion process, wherein the heat of the extrusion process leads to crosslinking or wherein a chemical species that leads to crosslinking (e.g., water/moisture, multifunctional crosslinking agent, etc.) is introduced into the extruder at suitable point along the extruder barrel.

In certain embodiments, crosslinkable compositions in accordance with the present invention are used to form a coating on a medical device component. For instance, in some embodiments, a crosslinkable composition in accordance with the present invention may be applied to a medical device component and cured, for example by overmolding, by heating, by exposure to radiation, or by admixing with a chemical species that leads to crosslinking (e.g., water/moisture, a multifunctional crosslinking agent, organometallic complex, etc.)

In certain embodiments, crosslinkable compositions in accordance with the present invention are used to attach two or more medical device components to one another. For instance, in some embodiments, a crosslinkable composition in accordance with the present invention is positioned between two or more medical device components and cured, for example, by heating, by exposure to radiation, or by admixing with a chemical species that leads to crosslinking (e.g., water/moisture, a multifunctional crosslinking agent, etc.) For example, crosslinkable compositions in accordance with the present invention may be used to attach a silicone component to a silicone component, to attach a silicone component to a polyurethane component, to attach a polyurethane component to a polyurethane component, to attach a polyisobutylene polymer (e.g., a polyisobutylene homopolymer or copolymer, for instance, a block copolymer, polyurethane, polyurea, polyurethane/urea, and so forth) component to a polyisobutylene polymer component, to attach a polyisobutylene polymer component to a silicone component, to attach a polyisobutylene polymer component to a non-polyisobutylene polyurethane component, and so forth. In many of these embodiments, the crosslinkable compositions will contain a polymeric segment that is common to each component to maximize compatibility (e.g., a polydimethylsiloxane segment when bonding a silicone component, a polyisobutylene segment with bonding a polyisobutylene polymer component, etc.)

More generally, in accordance with various aspects of the invention, implantable and insertable medical devices are provided, which contain one or more polymeric regions containing one or more crosslinked polyisobutylene polymers (e.g., one or more crosslinked polyisobutylene urethane, urea or urethane/urea copolymers). As used herein, a "polymeric region" is a region (e.g., an entire device, a device component, a device coating layer, an adhesive region with a device, etc.) that contains polymers, for example, from 50 wt % or less to 75 wt % to 90 wt % to 95 wt % to 97.5 wt % to 99 wt % or more polymers.

As indicated above, in some embodiments, the polymeric regions of the present invention correspond to an entire medical device. In other embodiments, the polymeric regions correspond to one or more portions of a medical device. For instance, the polymeric regions can be in the form of medical device components, in the form of one or more fibers which are incorporated into a medical device, in the form of one or more polymeric layers formed over all or only a portion of an underlying medical device or device component, in the form of an adhesive region that attaches two or more other medical device components to one another, and so forth.

Examples of medical devices for the practice of the present invention include implantable or insertable medical devices, for example, implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, cardiac systems including implantable pacemaker systems, implantable cardioverter-defibrillators (ICD's), and cardiac resynchronization and defibrillation (CRDT) devices, including polymeric components for leads including lead insulation, outer body insulation, and components for the foregoing implantable electrical stimulation systems, stents (including coronary vascular stents, peripheral vascular stents, cerebral, urethral, ureteral, biliary, tracheal, gastrointestinal and esophageal stents), stent coverings, stent grafts, vascular grafts, valves including heart valves and vascular valves, abdominal aortic aneurysm (AAA) devices (e.g., AAA stents, AAA grafts, etc.), vascular access ports, dialysis ports, embolization devices including cerebral aneurysm filler coils (including Guglilmi detachable coils and metal coils), embolic agents, tissue bulking devices, catheters (e.g., renal or vascular catheters such as balloon catheters and various central venous catheters), guide wires, balloons, filters (e.g., vena cava filters and mesh filters for distil protection devices), septal defect closure devices, myocardial plugs, patches, ventricular assist devices including left ventricular assist hearts and pumps, total artificial hearts, shunts, anastomosis clips and rings, and tissue engineering scaffolds for cartilage, bone, skin and other in vivo tissue regeneration (e.g., porous scaffolds, electrospun films and membranes for tissue integration), urethral slings, hernia "meshes", artificial ligaments, orthopedic prosthesis, one grafts, spinal disks, dental implants, biopsy devices, as well as any coated substrate (which can comprise, for example, metals, polymers, ceramics and combinations thereof) that is implanted or inserted into the body.

In certain preferred embodiments, crosslinkable polyisobutylene polymers in accordance with the present invention may be used to form lead insulation components through which at least one conductor extends, including single-lumen and multi-lumen extrusions and tubular (tube-shaped) insulation layers, and inner and outer coatings for implantable electrical leads, or they may be used to form various other lead components (e.g., O-ring seals, drug delivery collars, lead tip materials, lead terminal pins, headers, etc.).

In certain embodiments, crosslinkable polyisobutylene polymers in accordance with the present invention may be used to form polymeric components of electronic signal generating/sensing components, examples of which include implantable pulse generators, implantable cardioverter-defibrillators (ICDs) and implantable cardiac resynchronization therapy (CRT) devices. Such electronic signal generating/sensing components may be used, for example, in conjunction with right ventricular lead systems, right atrial lead systems, and left atrial/ventricular lead systems and may be used to treat, for example, bradycardia, tachycardia (e.g., ventricular tachycardia) or cardiac dyssynchrony in a vertebrate subject (including humans, pets and livestock). Specific examples of such polymeric components include connectors (plugs) for "cans" (i.e., housings that contain electronic signal generating/sensing components), seals (coatings) for cans, drug delivery collars, delivery collars, plugs, passive fixation tip/tines, tip assemblies, molded seals, and suture sleeves, among many other applications.

Single-lumen and multi-lumen components may be formed, for example, by reactive extrusion. Discrete components such as O-ring seal, lead tip materials, lead terminal pins, headers, connectors (plugs), drug delivery collars, drug delivery plugs, or any other component currently molded from silicone or polyurethane, among others, may be formed, for example, by molding.

Low Durometer materials (e.g., 40 A to 70 A Shore hardness) may be preferred for components such as seals, neck joint, passive fixation tines. Such low Durometer materials may be formed using any of the above crosslinkable polyisobutylene polymers including urethane, urea and urethane/urea copolymers with little or no chain extension in presence of a cross-linker and a crosslinking agent. Medium Durometer materials (e.g., 70 A to 85 A Shore Hardness) may be preferred for components such as lead tips, and connectors amongst others. High Durometer materials (e.g., 85 A to 75 D Shore Hardness scale) may be preferred for components such as terminal pins, device headers, etc.

Typical applications in leads where it is desirable to connect one component to another using the adhesives of the invention include various polymer-to-polymer and polymer-to-metal joints, more particularly, header to set screw seals, port seals, terminal ring seals, drug collar bonds, all joints in the IS-4 terminal, the pigtail joint cable, polyurethane boot to terminal and potting, tip to tubing-neck region (Reliance IS-1 and IS-4), terminal region in pacing leads, SST terminal ring to seal in pacing leads, bonds with the titanium (Reliance IS-1 and IS-4), bonds in the terminal and in the distal transition regions, header to titanium cans, and so forth.

Various known polyurethanes presently used in the medical device art (such as polyether, polyester, and polycarbonate based polyurethanes and/or their blends/copolymers with polydimethylsiloxane) can eventually exhibit environmental stress cracking upon insertion into a patient's body, due to the harsh (e.g., oxidative, hydrolytic, enzymatic, etc.) conditions that are encountered there. Where such polyurethanes are employed as lead insulation materials, such cracking can cause a breach in the insulation that allows bodily fluids to enter the lead and form shorts, for example, between the conductor(s) and/or the electronic components that generate current through the conductor(s). Moreover, slow corrosion of the metal conductor(s) within electrical leads is often encountered in the in vivo environment. The metal ions thus generated from the slow corrosion process are known to react with various insulation materials, including polyurethanes, causing metal ion oxidation (MIO) that can result in degradation and deterioration of the material. This can lead to rapid battery depletion and affect the ability of the device to reliably provide therapy.

The polyisobutylene urethane, urea and urethane/urea copolymers in accordance with the present invention, on the other hand, are believed to possess enhanced biostability and biocompatibility. In this regard, it is believed that the polyisobutylene segments within the copolymer of the invention are highly resistant to degradation (e.g., oxidative, hydrolytic, enzymatic, metal ion, etc.) relative to known polyurethane soft segments such as polyether, polyester, and polycarbonate based polyurethanes and/or their blends/copolymers with polydimethylsiloxane. Polyisobutylene is also known to have good barrier properties and is biocompatible.

Because the materials of the invention have good structural and electrical characteristics, good biostability and good biocompatibility, in certain embodiments, a single extrusion may be employed as a lead insulation material without the need for inner and outer coatings. In certain embodiments, a single extrusion may be formed which varies in Durometer along its length. For example, the extrusion may vary from 40 A at or near the distal tip (to provide flexibility for lead tip navigation) to 100 A at or near the proximal end of the extrusion (to provide stiffness for lead advancement). In one specific example, the Durometer of the material may be changed by changing the relative amounts of the polyisobutylene diol, optional non-polyisobutylene diol, diisocyanate and chain extender during the course of reactive extrusion. Durometer can also be changed by changing the amount of crosslinking agent that is provided during the course of extrusion.

As noted above, in addition to crosslinked polyisobutylene polymers, the polymeric regions for use in the medical devices of the present invention may optionally contain one or more supplemental agents.

For example, in some embodiments, an organically modified silicate is blended with the polymers forming the polymeric region as a supplemental agent. Such an agent may act to create a tortuous pathway for moisture thereby decreasing the moisture permeability of the region. Moreover, such silicates may maintain the strength and increase the modulus of the material. Supplemental agents further include agents such as alumina, silver nanoparticles, and silicate/alumina/silver nanoparticle composites. Supplemental agents further include fluoroscopy markers such as calcium tungstate and other tungsten based compositions, among others.

In some embodiments, one or more therapeutic agents are included beneath, within (e.g., blended with), or attached to (e.g., covalently or non-covalently bound to) polymeric regions in accordance with the invention. "Therapeutic agents," "drugs," "pharmaceutically active agents," "pharmaceutically active materials," and other related terms may be used interchangeably herein.

A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine) (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists, (hh) non-fouling, protein resistant agents such as polyethyelene glycol and (ii) prohealing agents.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid SOD (orgotein) and SOD mimics, verteporfin, rostaporfin, AGI 1067, and M40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), sirolimus, everolimus, tacrolimus, zotarolimus, biolimus, cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Where a therapeutic agent is present, a wide range of loadings may be used in conjunction with the medical devices of the present invention. Typical therapeutic agent loadings range, for example, from than 1 wt % or less to 2 wt % to 5 wt % to 10 wt % to 25 wt % or more of the polymeric region.

EXAMPLES

Example 1

A polyisobutylene (PIB) derivative with terminal unsaturation having a number average molecular weight ranging from 100 to 100,000 Daltons is initially synthesized, for example, selected from the following:

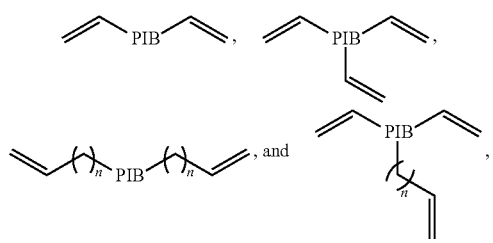

where n is an integer ranging from 1 to 50. The PIB derivative with terminal unsaturation is then extruded, molded (e.g., injection molded), or applied on or between two or more components to be bonded or joined, either by itself or with a suitable crosslinking agent, such as a UV initiator (e.g., benzophenone, benzoyl peroxide, AIBN, etc.) or a thermal initiator (e.g., a peroxide such as dicumyl peroxide) or an organometallic catalyst (e.g., a platinum catalyst) or any other known cross-linking agent. The resulting composition is then crosslinked using heat or using radiation (e.g., UV-Visible light, electron beam, gamma beam, laser irradiation, etc.), moisture or a metal catalyst, either at room temperature or elevated temperature.

Example 2

A polyisobutylene (PIB) derivative having a number average molecular weight ranging from 100 to 100,000 Daltons with suitable terminal reactive groups is initially synthesized, for example, selected from the following:

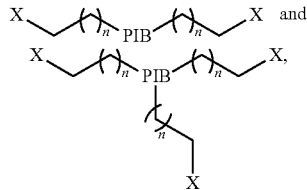

where n is an integer ranging from 1 to 50, and X is selected from —OH, —NH$_2$, —COOH, —COOCH$_2$CH$_3$, —CHOCH$_2$ (epoxide), —N=C=O, —O[Si(R)$_2$O]$_m$H, where m ranges from 1 to 100 and R is lower alkyl (e.g., —CH$_3$, —C$_2$H$_5$, etc.), —OSi(R)$_3$ where R is lower alkoxy (e.g., acetoxy), —CH=CH$_2$, —CH≡CH, —OC(=O)C(CH$_3$)=CH$_2$, —OC(=O)C(H)=CH$_2$ and —OC(=O)OCH$_2$(CH$_2$)$_p$CH=CH$_2$, wherein p ranges from 1 to 10, as well as —O[Si(R)$_2$O]$_m$(CH$_2$)$_p$—CH=CH$_2$, —O[Si(R)$_2$O]$_m$—(CH$_2$)$_p$—C≡CH, —O[Si(R)$_2$O]$_m$[CH$_2$C(CH$_3$)$_2$]$_q$—(CH$_2$)$_p$—C≡CH and —O[Si(R)$_2$O]$_m$—[CH$_2$C(CH$_3$)$_2$]$_q$—(CH$_2$)$_p$CH=CH$_2$ where m ranges from 2 to 100, p ranges from 1 to 10 and q ranges from 2 to 25.

When X is, for example, —OH, —NH$_2$ or —COOH, an organic crosslinking agent with two or more terminal isocyanate as functional groups may be employed. The organic crosslinking agent may be, for example, aromatic or aliphatic (e.g., linear, branched or hyper-branched aliphatic) or a combination of the preceding. The crosslinking reaction may be carried out either at room temperature or at elevated temperature.

When X is, for example, —N=C=O an organic crosslinking agent with two or more terminal —OH, —NH$_2$ or —COOH groups may be employed. The organic crosslinking agent may be, for example, aromatic or aliphatic (e.g., linear, branched or hyper-branched aliphatic) or a combination of the preceding. The crosslinking reaction may be carried out either at room temperature or at elevated temperature.

When X comprises terminal unsaturation, for example, where X is —O[Si(R)$_2$O]$_n$, —CH=CH$_2$, —O[Si(R)$_2$O]$_m$—(CH$_2$)$_p$—CH=CH$_2$, —O[Si(R)$_2$O]$_m$—C≡(CH$_2$)$_p$—C≡CH, —O[Si(R)$_2$O]$_m$[CH$_2$C(CH$_3$)$_2$]$_q$—(CH$_2$)$_p$—C≡CH or —O[Si(R)$_2$O]$_m$[CH$_2$C(CH$_3$)$_2$]$_q$—(CH$_2$)$_p$CH=CH$_2$ where n ranges from 2 to 100, p ranges from 1 to 10 and q ranges from 2 to 25, or where X is —OC(=O)C(H)=CH$_2$, —OC(=O)C(CH$_3$)=CH$_2$, or —OC(=O)OCH$_2$(CH$_2$)$_p$CH=CH$_2$, wherein p ranges from 1 to 10, the crosslinking reaction may be carried out either in the presence or in the absence of a crosslinking agent, for instance, a UV initiator (e.g., benzophenone, benzoyl peroxide, AIBN, etc.), a thermal initiator (e.g., a peroxide such as dicumyl peroxide), or an organometallic catalyst (e.g., a platinum catalyst). The crosslinking reaction may be carried out using heat or using radiation (e.g., UV-Visible light, electron beam, gamma beam, laser irradiation, etc.), moisture or a metal catalyst, either at room temperature or elevated temperature.

Example 3

Procedures such as are described above in Examples 1 and 2 can be employed using a suitable polyisobutylene urethane, urea or urethane/urea copolymer (PIBPU) having a number average molecular weight ranging from 100 to 100,000 Daltons with terminal functional groups, for instance,

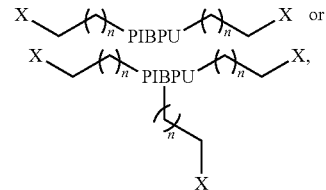

where n is an integer ranging from 1 to 50, and X is selected, for example, from —CH=CH$_2$, —(CH$_2$)$_p$CH=CH$_2$ where p ranges from 1 to 10, —CH≡CH, —O[Si(R)$_2$O]$_m$CH=CH$_2$ where m ranges from 1 to 100 and R is lower alkyl (e.g., —CH$_3$, —C$_2$H$_5$, etc.), —OC(=O)C(H)=CH$_2$ or —OC(=O)C(CH$_3$)=CH$_2$, or —O[Si(R)$_2$O]$_m$—(CH$_2$)$_p$—CH=CH$_2$, —O[Si(R)$_2$O]$_m$—(CH$_2$)$_p$—C≡CH, —O[Si(R)$_2$O]$_m$—[CH$_2$—C(CH$_3$)$_2$]$_q$—(CH$_2$)$_p$—C≡CH or —O[Si(R)$_2$O]$_m$—, [CH$_2$C(CH$_3$)$_2$]$_q$—(CH$_2$)$_p$CH=CH$_2$ where m ranges from 2 to 100, p ranges from 1 to 10 and q ranges from 2 to 25.

The crosslinking reaction may be carried out either in the presence or in the absence of a crosslinking agent, for instance, a UV initiator (e.g., benzophenone, benzoyl peroxide, AIBN, etc.), a thermal initiator (e.g., a peroxide such as dicumyl peroxide), or an organometallic catalyst (e.g., a platinum catalyst). The crosslinking reaction may be carried out using heat or using radiation (e.g., UV-Visible light, electron beam, gamma beam, laser irradiation, etc.), moisture or a metal catalyst, either at room temperature or elevated temperature.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a polymeric region that comprises:
    a crosslinked urethane, urea or urethane/urea copolymer
    a polyisobutylene segment; and
    a crosslinking agent residue, wherein the crosslinking agent residue includes a free radical initiator residue.

2. The medical device of claim 1, wherein said polymeric region is a coating or adhesive layer that is applied to a medical device component.

3. The medical device of claim 1, wherein said polymeric region is a molded or extruded medical device component.

4. The medical device of claim 1, wherein said medical device is selected from stent, a heart valve, an implantable electrical lead, a pacemaker, a defibrillator and a heart failure device.

5. The medical device of claim 1, wherein said polymeric region further comprises a therapeutic agent.

6. The medical device of claim 1, wherein said polymeric region further comprises a supplemental agent including fluoroscopy markers.

7. The medical device of claim 6, wherein in the fluoroscopy marker is calcium tungstate.

8. The medical device of claim 1, wherein said polymeric region further comprises a supplemental agent including at least one of organically modified silicate, alumina, silver nanoparticles, and silicate/alumina/silver nanoparticle composites.

9. The medical device of claim 1, wherein said polymeric region includes one or more fibers which are incorporated into a medical device component.

10. The medical device of claim 1, wherein the free radical initiator residue is a free radical thermal initiator residue.

11. The medical device of claim 1, wherein the free radical initiator residue is a free radical photoinitiator.

* * * * *